(12) United States Patent
Ito et al.

(10) Patent No.: US 8,460,261 B2
(45) Date of Patent: Jun. 11, 2013

(54) ABSORBENT ARTICLE

(75) Inventors: Yukihiro Ito, Kanonji (JP); Makoto Suekane, Kanonji (JP); Masataka Kinoshita, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 0 days.

(21) Appl. No.: 12/430,167

(22) Filed: Apr. 27, 2009

(65) Prior Publication Data

US 2009/0209927 A1    Aug. 20, 2009

Related U.S. Application Data

(62) Division of application No. 11/380,780, filed on Apr. 28, 2006.

(30) Foreign Application Priority Data

May 2, 2005   (JP) .................................. 2005-134648

(51) Int. Cl.
*A61F 13/15*   (2006.01)
*A61F 13/20*   (2006.01)

(52) U.S. Cl.
USPC ............. 604/385.14; 604/385.11; 604/385.01

(58) Field of Classification Search
USPC ............. 604/385.01, 385.11, 385.14, 385.16
See application file for complete search history.

(56) References Cited

U.S. PATENT DOCUMENTS

| | | | |
|---|---|---|---|
| 4,377,615 A | 3/1983 | Suzuki et al. | |
| 4,573,986 A * | 3/1986 | Minetola et al. | ............. 604/366 |
| 4,576,597 A | 3/1986 | Hlaban | |
| 4,761,322 A | 8/1988 | Raley | |
| 4,826,497 A | 5/1989 | Marcus et al. | |
| 5,591,150 A * | 1/1997 | Olsen et al. | ............. 604/385.23 |
| 5,599,339 A | 2/1997 | Horney | |

(Continued)

FOREIGN PATENT DOCUMENTS

| | | |
|---|---|---|
| CN | 1037646 | 12/1989 |
| CN | 1507844 | 6/2004 |

(Continued)

OTHER PUBLICATIONS

Japanese Notice of Reasons for Rejection dated Jan. 12, 2010, directed to counterpart Japanese Application No. 2005-134648; 3 pages (Partial English translation).

(Continued)

*Primary Examiner* — Michele M Kidwell
(74) *Attorney, Agent, or Firm* — Morrison & Foerster LLP

(57) ABSTRACT

An absorbent article in which a plurality of absorbent components is layered, and the absorbent component on top is peeled off after use. The article is configured to inhibit twisting or wrinkling during use. In the absorbent article, the upper absorbent component is layered on the skin-facing surface of the bottom absorbent component and peelably bonded by the temporal adhesive member. The bottom absorbent component has higher flexural rigidity than the upper absorbent component, and the compression recovery rate of the bottom absorbent component is also set so as to be higher than that of the upper absorbent component. It is thereby possible to prevent the bottom absorbent component from twisting and wrinkling when the upper absorbent component is placed against the discharge area, and after the upper absorbent component is peeled off, the volume of the bottom absorbent component is restored, and comfort during contact thereof with the discharge area is improved.

20 Claims, 10 Drawing Sheets

U.S. PATENT DOCUMENTS

| | | | |
|---|---|---|---|
| 5,658,269 | A | 8/1997 | Osborn, III et al. |
| 5,704,932 | A | 1/1998 | Hibbard |
| 5,720,738 | A | 2/1998 | Clark |
| 5,910,137 | A | 6/1999 | Clark et al. |
| 6,280,427 | B1 | 8/2001 | Maggiulli |
| 6,503,413 | B2 | 1/2003 | Uchiyama et al. |
| 6,620,144 | B1 | 9/2003 | Glasgow et al. |
| 2003/0109839 | A1* | 6/2003 | Costea et al. .................. 604/358 |
| 2005/0080391 | A1 | 4/2005 | Yoshimasa et al. |

FOREIGN PATENT DOCUMENTS

| | | |
|---|---|---|
| EP | 0 930 053 | 7/1999 |
| JP | 61-145528 | 9/1986 |
| JP | 63-77446 | 4/1988 |
| JP | 5-23366 | 2/1993 |
| JP | 5-49660 | 3/1993 |
| JP | 5-95973 | 4/1993 |
| JP | 7-13318 | 1/1995 |
| JP | 8-308872 | 11/1996 |
| JP | 9-512191 | 12/1997 |
| JP | 10-110372 | 4/1998 |
| JP | 11-332899 A | 12/1999 |
| JP | 2001-187084 A | 7/2001 |
| JP | 2003-038560 A | 2/2003 |
| JP | 2003-038562 A | 2/2003 |
| JP | 2003-038564 A | 2/2003 |
| JP | 2003-230592 | 8/2003 |
| JP | 2003-339761 | 12/2003 |
| JP | 2003-339765 | 12/2003 |
| JP | 2004-33348 | 2/2004 |
| JP | 2004-187732 | 7/2004 |
| WO | WO-95/29655 | 11/1995 |
| WO | WO-02/094160 A1 | 11/2002 |
| WO | WO-2004/019849 | 3/2004 |

OTHER PUBLICATIONS

Ito et al., U.S. Office Action mailed May 28, 2009, directed to U.S. Appl. No. 11/380,780; 8 pages.
Ito et al., U.S. Office Action mailed Mar. 17, 2010, directed to U.S. Appl. No. 11/380,780; 10 pages.
Ito, Y., et al. U.S. Office Action mailed Jan. 5, 2011, directed to U.S. Appl. No. 12/504,817; 9 pages.
Ito, Y., et al. U.S. Office Action mailed Jan. 7, 2011, directed to U.S. Appl. No. 12/504,861; 10 pages.
Ito, Y. et al., US Office Action mailed Oct. 29, 2010, directed to U.S. Appl. No. 11/380,780; 7 pages.
Ito, Y. et al., US Office Action mailed Oct. 4, 2010, directed to U.S. Appl. No. 12/430,174; 11 pages.
Ito, Y. et al., US Office Action mailed Oct. 29, 2010, directed to U.S. Appl. No. 12/430,175; 11 pages.
Japanese Office Action mailed Sep. 28, 2010, directed to Japanese Application No. 2005-134648; 2 pages.
Chinese Notification of the Second Office Action dated Jul. 29, 2011, directed to corresponding Chinese Patent Application No. 200610077369.8; 19 pages.
Japanese Office Action mailed Jan. 25, 2011, directed to Japanese Patent Application No. 2009-110170; 2 pages.
Japanese Office Action mailed Jan. 25, 2011, directed to Japanese Patent Application No. 2009-110171; 2 pages.
Ito, Y. et al., U.S. Office Action mailed Apr. 15, 2011, directed to U.S. Appl. No. 11/380,780; 7 pages.
Ito, Y. et al., U.S. Office Action mailed Mar. 30, 2011, directed to U.S. Appl. No. 12/430,174; 9 pages.
Ito, Y. et al., U.S. Office Action mailed Apr. 19, 2011, directed to U.S. Appl. No. 12/430,175; 9 pages.
Ito et al., U.S. Office Action mailed Jun. 24, 2011, directed to U.S. Appl. No. 12/504,817; 12 pages.
Ito et al., U.S. Office Action mailed Jun. 24, 2011, directed to U.S. Appl. No. 12/504,861; 12 pages.
Notification of the First Office Action dated Feb. 13, 2012, directed to Chinese Patent Application No. 200910138128.3; 6 pages.
Ito, Y. et al., U.S. Office Action mailed Dec. 12, 2011, directed to U.S. Appl. No. 12/504,861; 15 pages.
Ito et al., U.S. Office Action mailed May 18, 2012, directed to U.S. Appl. No. 11/380,780; 8 pages.
Ito et al., Office Action mailed May 8, 2012, directed to U.S. Appl. No. 12/430,174; 9 pages.
Interrogation mailed Mar. 6, 2012, directed to Japanese Application No. 2009-110170; 5 pages.
Ito et al., U.S. Office Action mailed Jun. 26, 2012, directed to U.S. Appl. No. 12/504,861; 13 pages.
Ito et al., U.S. Office Action mailed Sep. 19, 2012, directed to U.S. Appl. No. 12/504,817; 12 pages.
Ito et al., U.S. Office Action mailed Nov. 6, 2012, directed to U.S. Appl. No. 12/430,174; 10 pages.
Ito et al., U.S. Office Action mailed Feb. 1, 2013, directed to U.S. Appl. No. 12/504,861; 13 pages.
Ito et al., U.S. Office Action mailed Feb. 4, 2013, directed to U.S. Appl. No. 11/380,780; 8 pages.
Ito et al., U.S. Office Action mailed Feb. 14, 2013, directed to U.S. Appl. No. 12/430,174; 11 pages.
Ito et al., U.S. Office Action mailed Apr. 10, 2013, directed to U.S. Appl. No. 12/504,817; 13 pages.

* cited by examiner

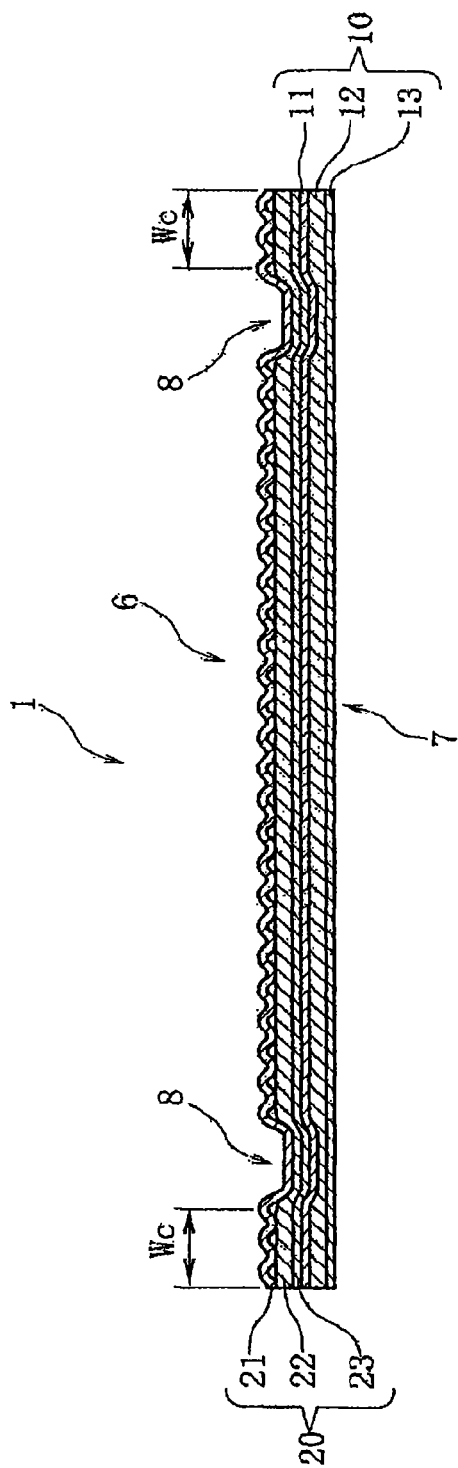
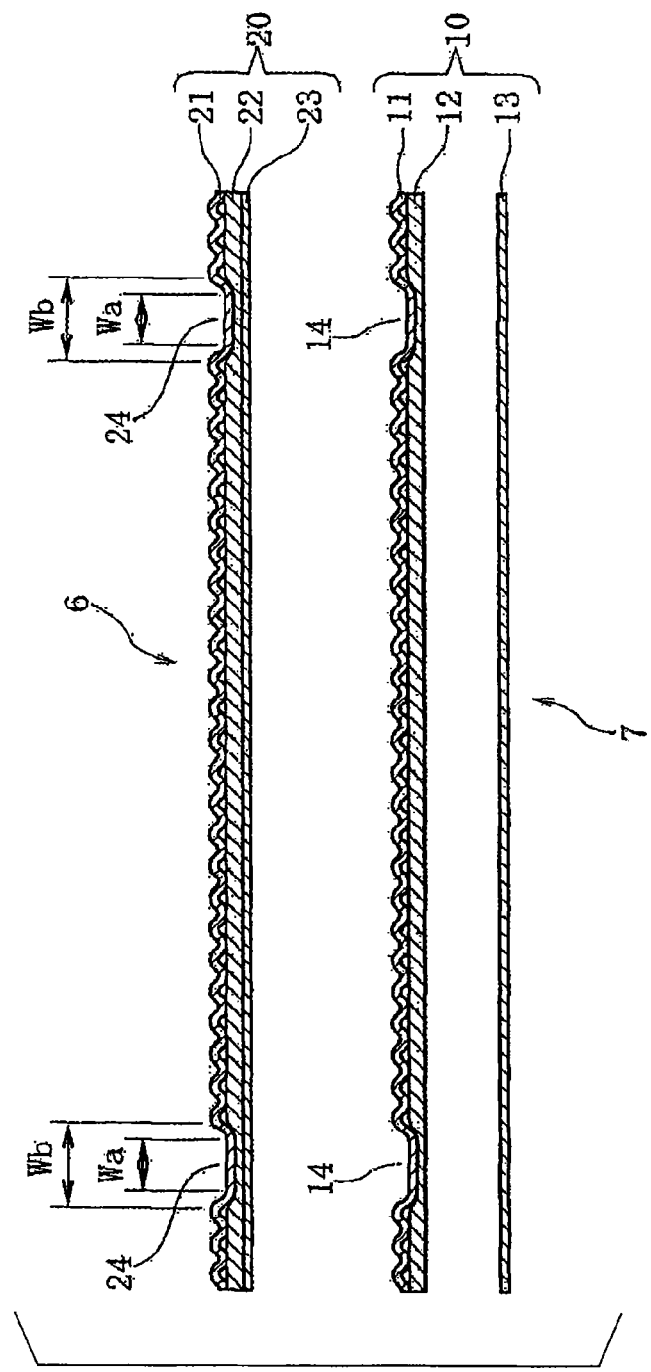
FIG. 2A
FIG. 2B

ABSORBENT ARTICLE

CROSS-REFERENCE TO RELATED APPLICATIONS

This is a Divisional application of U.S. patent application Ser. No. 11/380,780, filed Apr. 28, 2006 which claims priority under 35 U.S.C. §119 to Japanese Patent Application No. 2005-134648, filed May 2, 2005. The contents of each of these applications are hereby incorporated by reference in their entirety.

BACKGROUND OF THE INVENTION

1. Field of the Invention

The present invention relates to an absorbent article which is fixed to an undergarment and which absorbs vaginal discharge, menstrual bleeding, urine, or the like, and particularly relates to an absorbent article in which a plurality of absorbent components can be layered and bonded together, the absorbent component on top can be peeled off after use, and the absorbent component under the top component can be used.

2. Related Art

A composite menstrual sanitary product in which a plurality of composite absorbent sheets is layered so as to be able to peel apart is known as a menstrual sanitary product for absorbing blood that is discharged from a woman's vagina. When this composite menstrual sanitary product is used, the composite absorbent sheet that is the bottom layer is fixed to the inside surface of an undergarment, and the composite absorbent sheet that is the top layer is placed against the area of discharge. After the blood flow has been absorbed for a prescribed period of time by the top-layer composite absorbent sheet, the top-layer composite absorbent sheet is peeled off and discarded, and the composite absorbent sheet that is disposed under the discarded layer is placed against the area of discharge. The number of times that the absorbent product must be changed can thereby be reduced.

For example, in the composite absorbent sheets described in Japanese Laid-open Patent Application No. 2001-187084, the bottom-layer composite absorbent sheet and the top-layer composite absorbent sheet are each composed of a lining sheet, a surface film, and a liquid-absorbent sheet sandwiched between the lining sheet and the surface film. In each composite absorbent sheet, the aforementioned lining sheet is formed so as to be larger than the surface film, and the lining sheets of the top-layer composite absorbent sheet and bottom-layer composite absorbent sheet are bonded together by heat sealing or a pressure-sensitive adhesive layer.

The aforementioned lining sheets are bonded together along the periphery of the composite absorbent sheet, and an area is formed in a portion thereof in which there is no bonding. The top-layer composite absorbent sheet can easily be peeled from the bottom-layer composite absorbent sheet by inserting a finger into this area.

The conventional composite menstrual sanitary products described in Japanese Patent Application No. 2005-134648 and other publications use a stack of composite absorbent sheets having the same structure. Therefore, when the top-layer composite absorbent sheet is used after being placed against the discharge area, there is a tendency for kinks or wrinkles to form in the bottom-layer composite absorbent sheet as a result of body or undergarment movement. When the top-layer composite absorbent sheet is peeled off, the bottom-layer composite absorbent sheet adheres to the discharge area instead of the top-layer composite absorbent sheet. When the bottom-layer composite absorbent sheet is kinked or wrinkled at this time, the adhesion of the bottom-layer composite absorbent sheet to the discharge area is easily compromised. As a result, the article becomes uncomfortable to wear when the bottom-layer composite absorbent sheet is fitted, and there is also a risk of leakage of blood and the like.

When the top-layer composite absorbent sheet is used after being placed against the discharge area, the bottom-layer composite absorbent sheet is in a compressed state for a long period of time due to bodily pressure exerted on the top-layer composite absorbent sheet. The bottom-layer composite absorbent sheet is therefore likely to be in a crushed state due to the contamination of the top-layer composite absorbent sheet when this top-layer composite absorbent sheet is peeled off. As a result, the bottom-layer composite absorbent sheet becomes uncomfortable to touch when it is placed against the discharge area of the body, and the ability of the bottom-layer composite absorbent sheet to absorb liquids is diminished.

In the conventional composite menstrual sanitary products described in Japanese Laid-open Patent Application No. 2001-187084 and other publications, the top-layer composite absorbent sheet and the lining sheet of the bottom-layer composite absorbent sheet are bonded together. The top-layer composite absorbent sheet is therefore difficult to peel off when the bottom-layer composite absorbent sheet is fixed to the undergarment. As a result, there is a risk of the bottom-layer composite absorbent sheet being separated from the undergarment when the top-layer composite absorbent sheet is peeled off.

Since the bonding portion of the lining sheet is located at the edge of the composite menstrual sanitary product, this bonding portion can easily cause skin discomfort when it comes in contact with the skin during fitting.

The bottom-layer composite absorbent sheet and the top-layer composite absorbent sheet also have the same appearance, and are difficult to distinguish from each other. Therefore, with this type of composite menstrual sanitary product, when the user observes during fitting that the product has absorbed blood or the like and become contaminated, the user may be unable to correctly distinguish whether the top-layer composite absorbent sheet or the bottom-layer composite absorbent sheet has been used. This is likely to cause inconvenience in the sense that the user may peel off from the undergarment and discard both the top-layer composite absorbent sheet and the bottom-layer composite absorbent sheet regardless of the fact that the bottom-layer composite absorbent sheet has not been used, or may peel the product from the undergarment without preparing a replacement menstrual sanitary product, even though the bottom-layer composite absorbent sheet is being used.

SUMMARY OF THE INVENTION

An object of the present invention is to overcome the abovementioned drawbacks of the prior art and to provide an absorbent article whereby excessive twisting or wrinkling can be prevented, or the occurrence of a crushed state can be minimized in a bottom absorbent component such as a bottom-layer composite absorbent sheet, and the bottom absorbent component can be used in an optimal state when an upper absorbent component such as a top-layer composite absorbent sheet is in use.

Another object of the present invention is to provide an absorbent article whereby the upper absorbent component is easily separated from the bottom absorbent component.

Yet another object of the present invention is to provide an absorbent article that can be configured so that it is easy to visually distinguish the difference between the upper absorbent component and the bottom absorbent component.

A first aspect of the present invention is an absorbent article in which a plurality of absorbent components having a liquid-absorbent layer is layered together, wherein positioning-fixing means fixed to clothing is provided on the clothing-facing surface of a bottom absorbent component positioned in a bottom stage, at least one upper absorbent component is peelably bonded to the skin-facing surface of the bottom absorbent component, and the bottom absorbent component has higher flexural rigidity than the upper absorbent component when flexed in the longitudinal direction.

In the absorbent article of the present invention, the bottom absorbent component can easily be prevented from undergoing the same twisting or wrinkling as the upper absorbent component even with the body or undergarment moving when the upper absorbent component is used after being placed against the discharge area. It is therefore easy to cause the bottom absorbent component to adhere to the discharge area when the spent upper absorbent component is peeled off, and the fit comfort of the bottom absorbent component is improved.

Furthermore, in the present invention, a plurality of the upper absorbent components is provided, each upper absorbent component is peelably layered, and the flexural rigidity is higher in the bottom absorbent component than in the upper absorbent component disposed at the top.

When a plurality of upper absorbent components is provided, the bottom absorbent component is given a higher flexural rigidity than the absorbent component on top. This configuration makes it easier to minimize the occurrence of twisting or wrinkling in the bottom absorbent component that is used last.

When a plurality of upper absorbent components is provided, the absorbent component positioned between the top absorbent component and the bottom absorbent component may have a lower flexural rigidity than the top absorbent component. However, it is preferred in the present invention that the flexural rigidity be higher in any of the upper absorbent components that is positioned closer to the clothing than in any of the upper absorbent components that are positioned closer to the skin.

In the present invention, the flexural rigidity of the bottom absorbent component is increased by making the weight of the material constituting the bottom absorbent component greater than that of the upper absorbent component, or the flexural rigidity of the bottom absorbent component is increased by making the thickness of the bottom absorbent component greater than that of the upper absorbent component, for example.

In the present invention, the nonwoven cloth constituting the bottom absorbent component is heat treated and increased in thickness, and/or the thickness is increased by forming irregularities in the surface layer of the bottom absorbent component. The flexural rigidity of the bottom absorbent component can thereby be increased.

A second aspect of the present invention is an absorbent article in which a plurality of absorbent components having a liquid-absorbent layer is layered together, wherein positioning-fixing means fixed to a piece of clothing is provided on the clothing-facing surface of a bottom absorbent component positioned in a bottom stage, at least one upper absorbent component is peelably bonded to the skin-facing surface of the bottom absorbent component, and the compression recovery rate (RC value) of the bottom absorbent component is higher than that of the upper absorbent component.

A plurality of the upper absorbent components is also provided in this case, each upper absorbent component is peelably layered, and the compression recovery rate (RC value) is preferably higher in the bottom absorbent component than in the upper absorbent component disposed at the top. When a plurality of the upper absorbent components is provided, any of the upper absorbent components that is positioned closer to the clothing preferably has a higher compression recovery rate (RC value) than any of the upper absorbent components that is positioned closer to the skin.

In the present invention, the compression recovery rate (RC value) of at least one of the materials constituting the bottom absorbent component is preferably 40% or higher.

In the aspects of the present invention described above, when the upper absorbent component is peeled off, the thickness of the bottom absorbent component increases. When the compression recovery rate (RC value) thereof is within the aforementioned range, the overall thickness of the absorbent article during use of the upper absorbent component can be made as small as possible, and when only the bottom absorbent component is used, the thickness of the bottom absorbent component is restored, and the fit comfort of the bottom absorbent component against the vaginal opening or other discharge area can be improved.

A third aspect of the present invention is an absorbent article in which a plurality of absorbent components having a liquid-absorbent layer is layered together, wherein positioning-fixing means fixed to a piece of clothing is provided on the clothing-facing surface of a bottom absorbent component positioned in a bottom stage, at least one upper absorbent component is layered on the skin-facing surface of the bottom absorbent component, a plurality of layers is layered and fixed together in both the bottom absorbent component and the upper absorbent component, and a temporal adhesive member for temporarily fixing the bottom absorbent component and the upper absorbent component is formed in the area in which the plurality of layers of absorbent components are layered; wherein the adhesive strength of the temporal adhesive member between the absorbent components is weaker than the fixing strength between the layers constituting the bottom absorbent component and than the fixing strength between the layers constituting the upper absorbent component.

In the present invention described above, the absorbent components are composed of a plurality of layers layered together, and a temporal adhesive member is formed in the area in which the plurality of layers is layered together. Therefore, since the upper absorbent component, which is an aggregate of a plurality of layers, has a prescribed thickness when peeled from the bottom absorbent component, it becomes easy to separate the upper absorbent component from the bottom absorbent component. Since the upper absorbent component is also temporarily fixed to the bottom absorbent component in the area in which the plurality of layers is layered, it is less likely for the bottom absorbent component to bend and wrinkle when the upper absorbent component is peeled off.

In the present invention, the temporal adhesive member is preferably formed in a position towards the inside from the edge of the absorbent component. By not placing the temporal adhesive member at the edge, it becomes easy to prevent the temporal adhesive member portion from causing discomfort to the skin of the body.

The temporal adhesive member in the present invention is also preferably formed so as to have an excluded portion.

When the temporal adhesive member is formed so as to have an excluded portion, it becomes possible to reliably peel the upper absorbent component from the bottom absorbent component.

It is preferred in the present invention that the bottom absorbent component and the upper absorbent component each have four corners, and that the plane pattern of the temporal adhesive member be curved at the tip of each of the four corners.

When the temporal adhesive member formed at the corners has a curved pattern, the temporal adhesive member is difficult to peel off in the corners even when the excluded portion is used to apply peeling force in the longitudinal direction with respect to the upper absorbent component during wear. However, when a finger is inserted into the excluded portion, and the upper absorbent component is peeled upwards, since the peeling force is propagated along the curved pattern, it becomes possible to separate the temporary fixing at the corners without experiencing significant resistance.

It is also preferred that the upper absorbent component be partially compressed in the excluded portion. The compressed portion of the upper absorbent component makes it easy to insert a finger between the bottom absorbent component and the upper absorbent component, and makes it possible to firmly grasp the upper absorbent component in the excluded portion and peel the upper absorbent component off.

A configuration may be adopted in the present invention whereby non-fusible fibers are included in at least one surface selected from the skin-facing surface of the bottom absorbent component and the clothing-facing surface of the upper absorbent component, and the temporal adhesive member is pressed in the thickness direction, heated, and formed in a state in which the skin-facing surface and the clothing-facing surface are placed opposite each other.

When non-fusible fibers are positioned in the portion in which the bottom absorbent component and the upper absorbent component face each other, and the temporal adhesive member is formed in this portion, it becomes easy to peel the bottom absorbent component and upper absorbent component apart without an excessive bonding force being created by the temporal adhesive member.

It is also preferred in the present invention that the skin-facing surface of the bottom absorbent component and the skin-facing surface of the upper absorbent component differ in color from each other. An embossed pattern is also preferably formed in at least one surface selected from the skin-facing surface of the bottom absorbent component and the skin-facing surface of the upper absorbent component, and mutually different patterns are preferably provided on the skin-facing surfaces. This visually recognizable difference between the bottom absorbent component and the upper absorbent component may be evident in both color and pattern.

By adopting this type of configuration, it can be immediately determined visually which layer of absorbent components is being used even when the absorbent component is contaminated with discharge. The user is also less likely to be inconvenienced by mistakenly discarding an unused bottom absorbent component, forgetting to bring a replacement absorbent article to the washroom, or experiencing other inconveniences.

The present invention may also be configured so that at least one functional agent selected from the group consisting of an antimicrobial agent, a deodorant, and a fragrance is included in at least the bottom absorbent component.

When an antimicrobial agent, a deodorant, a fragrance, or other functional agent is included in the bottom absorbent component as well as in the upper absorbent component, it becomes easy to keep microorganisms from proliferating and creating an odor during use. Including the aforementioned functional agent can be effective for minimizing proliferation of microorganisms or odors particularly in the bottom absorbent component that is worn for the longest period of time. A tea leaf extract is included as an example of this type of functional agent.

It becomes easy to suppress the occurrence of twisting or wrinkling in the bottom absorbent component when the upper absorbent component is peeled off in an absorbent article in which a plurality of absorbent components is layered together. Comfort is thereby improved when the bottom absorbent component is fitted to the discharge area.

According to the present invention, when the upper absorbent component is peeled off, the volume of the bottom absorbent component is restored, the comfort of the bottom absorbent component when placed against the discharge area can be improved, and a high degree of liquid absorption can be demonstrated in the bottom absorbent component.

Furthermore, according to the present invention, the upper absorbent component can easily be peeled from the bottom absorbent component, and the bottom absorbent component is less prone to wrinkle or undergo other adverse effects when the upper absorbent component is peeled off.

BRIEF DESCRIPTION OF THE DRAWINGS

FIG. 2A is a sectional view along line II-II of the absorbent article shown in FIG. 1;

FIG. 2B is a separated sectional view of the separate absorbent components;

FIG. 6 shows the absorbent article according to a third embodiment of the present invention, wherein

DESCRIPTION OF THE PREFERRED EMBODIMENT

Figure 1:
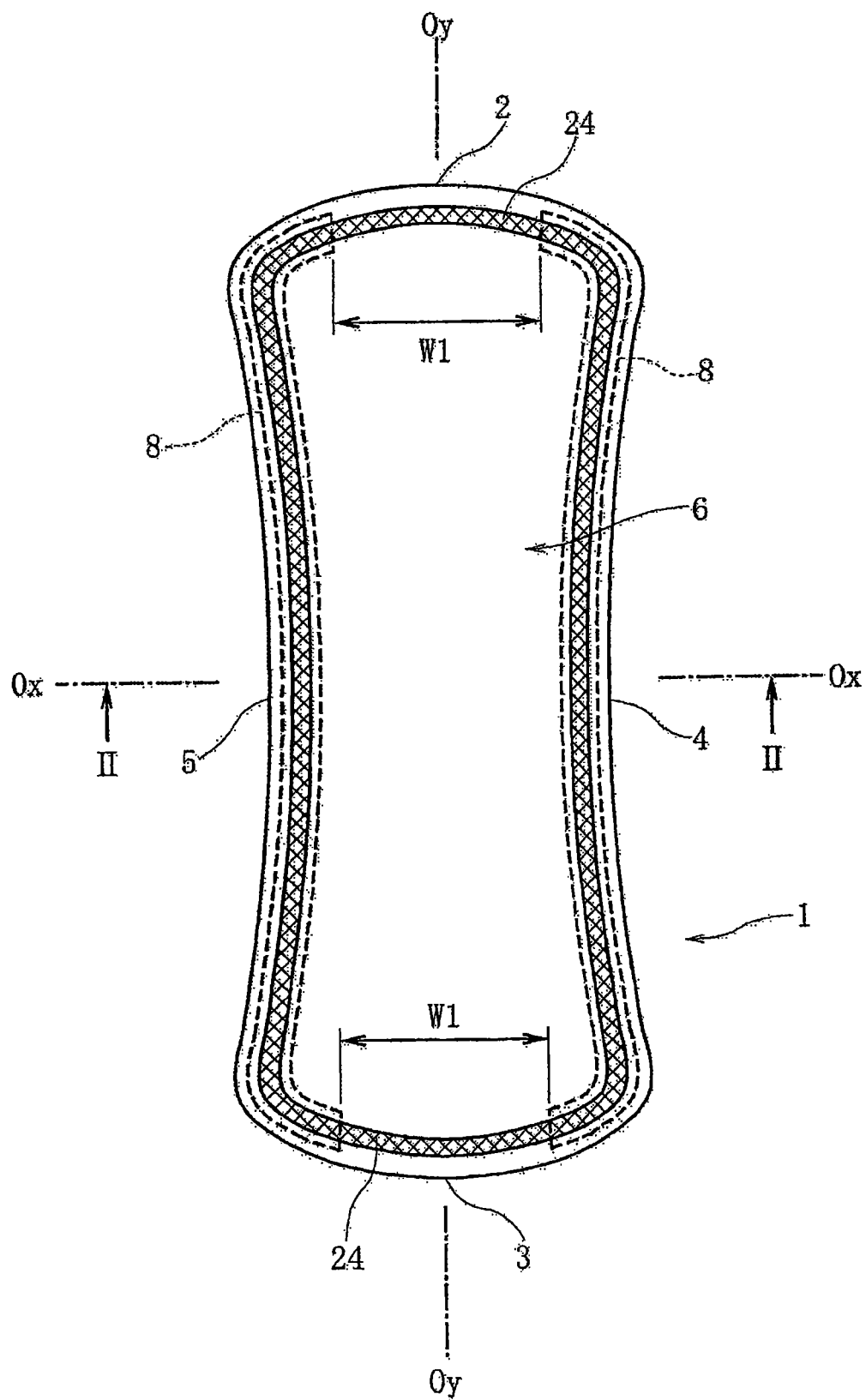
FIG. 1 is a plan view showing the absorbent article according to a first embodiment of the present invention as viewed from the skin-facing surface.

FIG. 1 is a plan view showing the absorbent article 1 according to a first embodiment of the present invention as viewed from the skin-facing surface; FIG. 2A is a sectional view along line II-II of the absorbent article shown in FIG. 1; and FIG. 2B is a separated sectional view of the separate absorbent components of the absorbent article 1.

The absorbent article 1 described hereinafter is used after being fixed as a panty liner to the inside surface of the crotch portion of an undergarment, and is used for the purpose of absorbing vaginal discharge, small amounts of blood, and the like. However, the absorbent article of the present invention may also be configured for use as a menstrual sanitary product for absorbing a relatively large quantity of blood, or as a urine-absorbent pad used for the purpose of absorbing urine.

The absorbent article 1 shown in FIG. 1 and FIG. 2A is bilaterally symmetrical about the boundary established by the vertical center line Oy. The absorbent article is also symmetrical about the boundary established by the horizontal center line Ox. FIG. 2A is a sectional view of the absorbent article 1 along the horizontal center line Ox. This absorbent article 1 has an elongated shape in which the longitudinal dimension, which is the dimension of the portion passed through by the vertical center line Oy, is greater than the transverse dimension, which is the dimension of the portion passed through by the horizontal center line Ox. The article is fitted so that the longitudinal direction is oriented in the anteroposterior direction between the legs of the body.

As shown in FIG. 1, the absorbent article 1 has a front edge 2 outward-curved towards the front; a back edge 3 outward-curved towards the back; and a right-side edge 4 and left-side edge 5 formed with a shape that curves inward so that the transverse dimension decreases towards the vertical center line. The side of this absorbent article 1 that faces the skin when fitted is the skin-facing surface 6, and the side that faces the undergarment or another piece of clothing is the clothing-facing surface 7. The sheets constituting the absorbent article 1 are referred to as "skin-facing" on the side towards the skin-facing surface 6, and as "clothing-facing" on the side towards the clothing-facing surface 7.

As shown in FIGS. 2A and 2B, this absorbent article 1 has a bottom absorbent component 10 and an upper absorbent component 20 that is layered on the skin side of the bottom absorbent component 10. The bottom absorbent component 10 is composed of a surface sheet 11, a middle sheet 12, and an article backing sheet 13 layered together. The upper absorbent component 20 is composed of a surface sheet 21, a middle sheet 22, and a back surface sheet 23 layered together.

The planar shape of the bottom absorbent component 10 is the same as the planar shape of the entire absorbent article 1 shown in FIG. 1, and the peripheral edge of the surface sheet 11, middle sheet 12, and article backing sheet 13 constituting the bottom absorbent component 10 has the same shape as the front edge 2, back edge 3, right-side edge 4, and left-side edge 5 of the absorbent article 1. The planar shape of the upper absorbent component 20 is the same as the planar shape of the entire absorbent article 1 shown in FIG. 1, and the peripheral edge of the surface sheet 21, middle sheet 22, and back surface sheet 23 constituting the upper absorbent component 20 has the same shape as the front edge 2, back edge 3, right-side edge 4, and left-side edge 5 of the absorbent article 1.

In the bottom absorbent component 10, the surface sheet 11 and the middle sheet 12 are bonded together by a rubber-based hot-melt adhesive applied in a spiral pattern or the like in an amount ($10 \text{ g/m}^2$, for example) that does not inhibit the transmission of liquid, and the surface sheet 11 and middle sheet 12 are also integrally fixed in a round seal 14. In the round seal 14, the surface sheet 11 and middle sheet 12 are heated and pressed together, the thermofusible fibers included in at least one sheet selected from the surface sheet 11 and the middle sheet 12 are melted, and the surface sheet 11 and middle sheet 12 are securely fixed to each other.

In the same manner, in the upper absorbent component 20, the surface sheet 21 and the middle sheet 22 are bonded together by a hot-melt adhesive applied in an amount that does not inhibit the transmission of liquid, and the middle sheet 22 and back surface sheet 23 are bonded together by a hot-melt adhesive. Furthermore, the surface sheet 21, middle sheet 22, and back surface sheet 23 are integrally fixed in a round seal 24. In the round seal 24, the surface sheet 21, middle sheet 22, and back surface sheet 23 are heated and pressed together, the back surface sheet 23 and the thermofusible fibers included in at least one sheet selected from the middle sheet 22 and the surface sheet 21 are melted, and the surface sheet 21, middle sheet 22, and back surface sheet 23 are securely fixed to each other.

In FIG. 1, the round seal 24 formed on the upper absorbent component 20 is indicated by a solid line. This round seal 24 is formed along the entire length of the external periphery of the upper absorbent component 20, and the round seal 24 is formed in a position that is at a distance inward from the front edge 2, back edge 3, right-side edge 4, and left-side edge 5 in the upper absorbent component 20. In the same manner, the round seal 14 is formed all the way around the bottom absorbent component 10, and this round seal 14 is formed in a position that coincides with that of the round seal 24 of the upper absorbent component 20, and is formed with the same width dimension as the round seal 24.

Furthermore, the upper absorbent component 20 is layered on the skin side of the surface sheet 11 of the bottom absorbent component 10, and the pre-integrated surface sheet 11 and middle sheet 12, as well as the pre-integrated upper absorbent component 20 are temporarily fixed to each other by a temporal adhesive member 8 so as to be able to separate. The temporal adhesive member 8 is formed by layering the upper absorbent component 20 on the surface sheet 11, and heating and pressing all of the layers except the article backing sheet 13. The temporal adhesive member 8 is indicated by a dashed line in FIG. 1. However, as shown in FIG. 2A, the area in which the temporal adhesive member 8 is formed is recessed in concave fashion in the skin-facing surface 6 of the absorbent article 1.

As shown in FIG. 1, the temporal adhesive member 8 is formed along the right-side edge 4 and left-side edge 5 of the absorbent article 1, but in the front edge 2 and back edge 3, the temporal adhesive member 8 is not formed in an area that extends laterally over a distance W1 about the vertical center line Oy, and the area W1 is the excluded portion of the temporal adhesive member 8.

Figure 5:
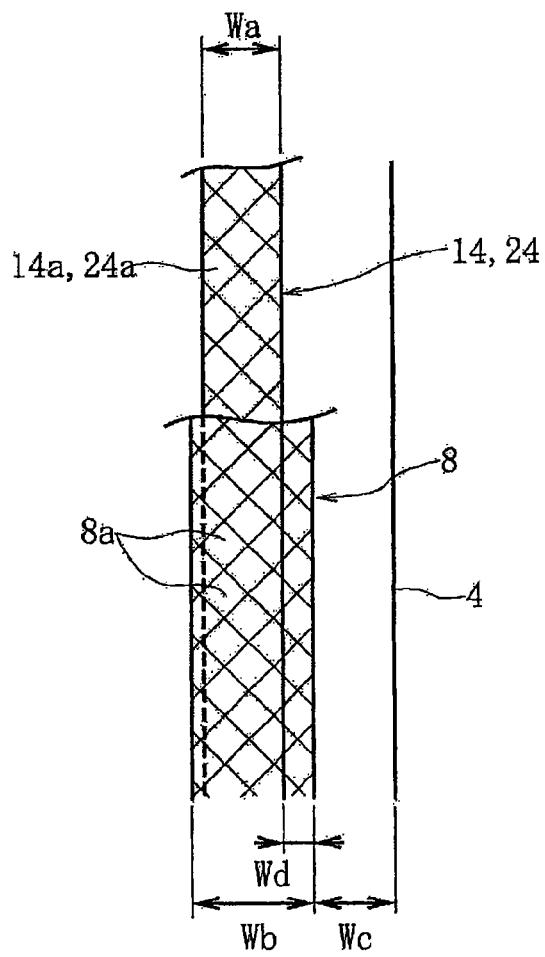
FIG. 5 is a plan view for describing the positional relationship between a round seal and the temporal adhesive member.

In FIG. 2B, the width dimension of the round seal 14 formed in the bottom absorbent component 10, and the width dimension of the round seal 24 formed in the upper absorbent component 20 are each indicated by the reference symbol Wa, and the width dimension of the temporal adhesive member 8 is indicated by the reference symbol Wb. FIG. 5 is a partial plan view showing an enlarged view of the round seals 14 and 24 and the temporal adhesive member 8. Also in FIG. 5, the width dimensions of the round seals 14 and 24 are indicated by the reference symbol Wa, and the width dimension of the temporal adhesive member 8 is indicated by the reference symbol Wb.

The area in which the round seals 14 and 24 are formed and the area in which the temporal adhesive member 8 is formed coincide with each other, and the width dimension Wb of the temporal adhesive member 8 is greater than the width dimension Wa of the round seals 14 and 24. The width dimension Wa of the round seals 14 and 24 is about 2 mm, for example, and the width dimension Wb of the temporal adhesive member 8 is about 3 mm, for example.

The bonding strength between the bottom absorbent component 10 and the upper absorbent component 20 in the temporal adhesive member 8 is set so as to be less than the bonding strength of the round seal 14 between the surface sheet 11 and the middle sheet 12 of the bottom absorbent component 10. The bonding strength of the temporal adhesive member 8 is also set so as to be less than the bonding strength of the round seal 24 between the layers that include the surface sheet 21, the middle sheet 22, and the back surface sheet 23 of the upper absorbent component 20.

Figure 4:
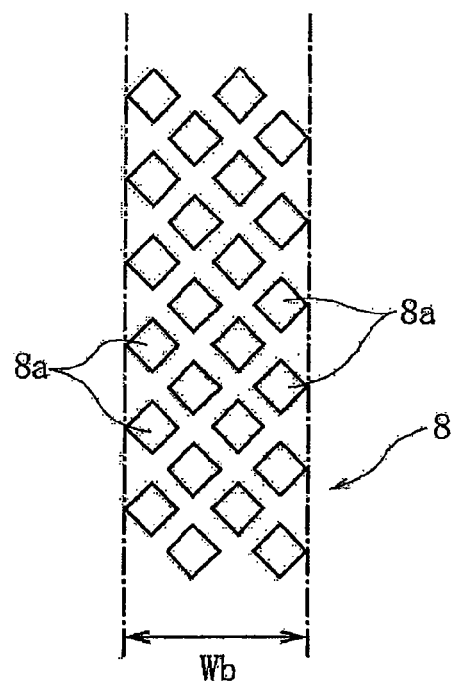
FIG. 4 is an enlarged plan view showing details of a pattern in a compressed portion of the temporal adhesive member.

FIG. 4 shows the details of the pressed pattern on the temporal adhesive member 8. The seal pattern is not shown in FIG. 5 and other drawings. In the temporal adhesive member 8 as shown in FIG. 4, square pressure portions 8a are formed at a 45-degree angle with respect to the longitudinal direction of the absorbent article 1, and the pressure portions 8a are spaced apart from each other and arranged to form rows at a 45-degree angle. In the temporal adhesive member 8, the surface sheet 11, the middle sheet 12, and the upper absorbent component 20 are heated and pressed together in the pressure portions 8a, the pressure portions 8a are concavely shaped in the skin-facing surface, and the pressure portions 8a function as joints between the surface sheet 11 and the upper absorbent component 20.

As shown in FIG. 5, the pattern of the pressure portions 14a and 24a of the round seal 14 that joins together the surface sheet 11 and middle sheet 12 of the bottom absorbent component 10, and the pattern of the round seal 24 that fixes the layers in the upper absorbent component 20, although not shown in detail in the drawing, are the same as the pattern of the pressure portions 8a shown in FIG. 4. The dimensions and arrangement pitch of the pressure portions 8a of the temporal adhesive member 8 may be the same as or different from the dimensions and arrangement pitch of the pressure portions 14a and 24a of the round seals 14 and 24. For example, the length of one side of the pressure portions 8a and the pressure portions 14a and 24a is about 0.2 to 1 mm, and the interval between the edges of adjacent pressure portions is about 0.2 to 1 mm.

The round seal 14 is formed by hot-pressing the surface sheet 11 and middle sheet 12 sandwiched between a roll having a smooth external periphery and a roll on which protrusions are formed that correspond to the pattern of the pressure portions 14a. The round seal 24 is formed by hot-pressing the upper absorbent component 20 sandwiched between a roll having a smooth external periphery and a roll on which protrusions are formed that correspond to the pattern of the pressure portions 24a. In the same manner, the temporal adhesive member 8 is formed by hot-pressing the surface sheet 11, middle sheet 12, and upper absorbent component 20 sandwiched between a roll having a smooth external periphery and a roll on which protrusions are formed that correspond to the pattern of the pressure portions 8a.

The two layers that include the surface sheet 11 and the middle sheet 12 are the only materials that are sandwiched between the rolls when the round seal 14 is formed, and the three layers that constitute the upper absorbent component 20 are the only materials that are sandwiched between the rolls when the round seal 24 is formed. In contrast, a total of five layers are sandwiched between the rolls when the temporal adhesive member 8 is formed. Furthermore, as previously mentioned, the width dimension Wa of the round seals 14 and 24 is less than the width dimension Wb of the temporal adhesive member 8. Accordingly, the compression force applied to the pressure portions 8a of the temporal adhesive member 8 is less than the compression force applied to the pressure portions 14a and 24a of the round seals 14 and 24 if the size and pitch of the pressure portions 14a and 24a of the round seals 14 and 24, and the size and pitch of the pressure portions 8a of the temporal adhesive member 8 are the same, and the pressing force and heating temperature between the rolls during processing are also the same.

It therefore becomes possible to set the strength of the bond between the surface sheet 11 and the middle sheet 12 created by the round seal 14, as well as the strength of the bond between the layers of the upper absorbent component 20 created by the round seal 24, to be sufficiently greater than the strength of the bond between the surface sheet 11 and the back surface sheet 23 created by the temporal adhesive member 8 even when the round seals 14 and 24 and the temporal adhesive member 8 are processed under the same conditions.

It is preferred that at least one sheet selected from the surface sheet 11 positioned on the skin side of the bottom absorbent component 10, and the back surface sheet 23 positioned on the clothing side of the upper absorbent component 20 have a thermal-adhesive material, and that at least one of these components include a non-fusible material.

The surface sheet 11 and the back surface sheet 23 are adhesively bonded to each other by the adhesive force of the thermal-adhesive material that is demonstrated when the temporal adhesive member 8 is formed. However, when non-fusible fibers are included in this adhesion surface, the surface sheet 11 and back surface sheet 23 can be prevented from being fused together too strongly by the temporal adhesive member 8, and it becomes easy to peel the upper absorbent component 20 from the bottom absorbent component 10. For example, the back surface sheet 23 is formed from a polyethylene resin film or other thermal-adhesive resin; the surface sheet 11 is formed from cotton, wood pulp, or other natural fibers, or is formed solely from non-fusible fibers such as rayon or other regenerated cellulose fibers; or the surface sheet 11 is formed by mixing the non-fusible fibers with thermofusible fibers. It is preferred in this case that the non-fusible fibers be included in an amount of 50% mass or higher in the surface sheet 11, and that the remainder be composed of fusible fibers.

As shown in FIG. 2A, the temporal adhesive member 8 is formed in a position at a distance Wc inward from the right-side edge 4 and the left-side edge 5. Specifically, any of the round seals 14 and 24 and the temporal adhesive member 8 may be formed in an area that extends over the distance Wc. The distance Wc is preferably 1 mm or greater, and more preferably 2 mm or greater.

As shown in FIG. 5, the temporal adhesive member 8 is preferably formed so as to protrude more towards the edge (the right-side edge 4, for example) of the absorbent article 1 than the round seals 14 and 24. In this case, none of the seal is disposed in the area that extends over a width dimension Wc towards the inside from the edge (the right-side edge 4, for example) of the absorbent article 1, only the temporal adhesive member 8 is disposed in the area that extends over the width dimension Wd towards the inside, and the round seals 14 and 24 and the temporal adhesive member 8 overlap further towards the inside. Therefore, since the area that extends from the edge over the width dimension Wc is flexible, and the rigidity increases in stages towards the inside, skin discomfort is less likely to occur when the edge touches the skin of the body.

The width dimension W1 of the excluded portion of the temporal adhesive member 8 shown in FIG. 1 is set to 5 to 30 mm so that a finger can be inserted into the excluded portion between the surface sheet 11 of the bottom absorbent component 10 and the back surface sheet 23 of the upper absorbent component 20.

After the upper absorbent component 20 and the surface sheet 11 and middle sheet 12 constituting the bottom absorbent component 10 are temporarily fixed by the temporal adhesive member 8, the article backing sheet 13 is fixed by a hot-melt adhesive to the clothing-facing surface of the middle sheet 12 of the bottom absorbent component 10. The bonding strength of the hot-melt adhesive between the middle sheet 12 and the article backing sheet 13 is set so as to be higher than the bonding strength of the temporal adhesive member 8 between the bottom absorbent component 10 and the upper absorbent component 20.

A pressure-sensitive adhesive layer as a positioning-fixing means is provided on the clothing-facing surface of the article backing sheet 13, and a release sheet is provided for protecting the pressure-sensitive adhesive layer before the absorbent article 1 is used. The strength with which the article backing sheet 13 and the undergarment are adhesively fixed together by the pressure-sensitive adhesive is set so as to be higher than the strength with which the bottom absorbent component 10 and the upper absorbent component 20 are bonded to each other by the temporal adhesive member 8.

The strength with which the article backing sheet 13 and the undergarment are adhesively fixed together is set so as to be less than the bonding strength between the surface sheet 11 and the middle sheet 12 in the bottom absorbent component 10, as well as the bonding strength between the middle sheet 12 and the article backing sheet 13.

The pressure-sensitive adhesive provided as the positioning-fixing means on the clothing-facing surface of the article backing sheet 13 is a hot-melt-type adhesive, and any one type or combination of two or more types selected from a styrene-isoprene-styrene copolymer, a styrene-butadiene-styrene copolymer, a styrene-ethylene-butadiene-styrene copolymer, and a styrene-butadiene copolymer can be used. The adhesive may be applied in any pattern such as a striped or dotted pattern, and the amount applied is in the range of 10 to 100 g/m$^2$. The fixing strength with respect to the undergarment is preferably 1 N/cm$^2$ or higher.

The aforementioned fixing strength is a value measured after affixing the article backing sheet 13 to the measuring unit of a "PICMA tack tester IMC-1567" manufactured by Imoto Machinery Co., Ltd., and applying pressure for two seconds.

At least one sheet selected from the surface sheet 11 and the middle sheet 12 of the bottom absorbent component 10 is hydrophilic and is capable of absorbing and retaining liquid. In the same manner, at least one sheet selected from the surface sheet 21 and the middle sheet 22 of the upper absorbent component 20 is hydrophilic and is capable of absorbing and retaining liquid.

For example, the middle sheet 12 and the middle sheet 22 demonstrate liquid absorption capability; are nonwoven cloths formed from cotton, wool, wood pulp, or other hydrophilic natural fibers; and are, for example, spunlace nonwoven cloths. Alternatively, the abovementioned sheets are spunlace nonwoven cloths that include hydrophilized synthetic resin fibers, rayon fibers, or other hydrophilic regenerated cellulose fibers. A through-air nonwoven cloth may also be used that is formed from hydrophilized synthetic resin fibers. A hydrophilic air-laid nonwoven cloth may be used in which pulp fibers are layered by an air-laying method and bonded together by a binder, or an air-laid nonwoven cloth may be used that includes regenerated cellulose fibers or synthetic resin fibers besides pulp fibers as the middle sheet 12 and middle sheet 22. A super-absorbent polymer (SAP) may also be added to the middle sheet 12 and middle sheet 22.

The surface sheets 11 and 21 are preferably capable of transmitting liquid to the middle sheets 12 and 22, and a spunlace nonwoven cloth or through-air nonwoven cloth may be used therein as a hydrophilic nonwoven cloth. These sheets may also be formed from a resin film that has numerous liquid-permeable pores.

A configuration may also be adopted in which the surface sheet 11 constituting the bottom absorbent component 10 and the surface sheet 21 constituting the upper absorbent component 20 are omitted, the bottom absorbent component 10 is formed only by the middle sheet 12 and article backing sheet 13, and the upper absorbent component 20 is composed solely of the middle sheet 22 and back surface sheet 23.

The article backing sheet 13 and the back surface sheet 23 are impermeable to liquid and are formed from a polyethylene resin film, a polypropylene resin film, a cellophane resin film, or the like. The article backing sheet 13 and the back surface sheet 23 are preferably formed from an air-permeable, liquid-impermeable resin film in which minute air pores are formed for transmitting air. The film is obtained by mixing in numerous minute fillers and stretching the product.

An SMS composite nonwoven cloth, in which a tri-layer nonwoven cloth composed of spunbonded nonwoven cloth, melt-blown nonwoven cloth, and spunbonded nonwoven cloth formed from polypropylene resin fibers is bonded by a heat tool, may be used as the article backing sheet 13 or the back surface sheet 23. Alternatively, a composite nonwoven cloth may be used in which an SMS composite nonwoven cloth, a melt-blown nonwoven cloth, and an SMS composite nonwoven cloth are layered and heat-tooled. These nonwoven cloths preferably have a weight of 15 to 40 g/m$^2$. Furthermore, the article backing sheet 13 or back surface sheet 23 may be formed from a laminate of the aforementioned nonwoven cloths with a resin film.

Particularly since the bottom absorbent component 10 is layered under the upper absorbent component 20, air permeability with the outside of the undergarment is easily inhibited, and moldering is a concern when the article is worn for a long period of time during summer or in another hot and humid environment. The aforementioned air-permeable nonwoven cloth is therefore preferred for use as the back surface sheet 23 used in the upper absorbent component 20. Since the aforementioned nonwoven cloth is flexible in comparison with a resin film, the absorbent article 1 as a whole is unlikely to acquire a rigid feel even when a back surface sheet 23 that is a nonwoven cloth is positioned in the middle of the absorbent article 1.

The bottom absorbent component 10 composed of the surface sheet 11, middle sheet 12, and article backing sheet 13, and the upper absorbent component 20 composed of the surface sheet 21, middle sheet 22, and back surface sheet 23 have different characteristics from each other. First, the flexural rigidity in the longitudinal direction is higher in the bottom absorbent component 10 than in the upper absorbent component 20 when measured independently in the bottom absorbent component 10 and the upper absorbent component 20. Second, in addition to the aforementioned rigidity difference, or irrespective of rigidity, the compression recovery rate when compressed in the thickness direction is higher in the bottom absorbent component 10 than in the upper absorbent component 20 when measured independently in the bottom absorbent component 10 and the upper absorbent component 20.

The abovementioned flexural rigidity may be measured using a No. 311 Gurley-type stiffness tester manufactured by Yasuda Seiki Seisakusho (Ltd.). A sample is created in which the bottom absorbent component 10 and upper absorbent component 20 are cut so that the width dimension in the direction along the horizontal center line Ox is 25 mm and the length dimension in the direction along the vertical center line Oy is 38 mm in the area in which the round seals 14 and 24 are not formed, and measurement is performed using the aforementioned tester so that the longitudinal direction is the flexing direction. The Gurley flexural rigidity of the bottom absorbent component 10 is preferably higher by at least 0.05 N per 25 mm of width than the Gurley flexural rigidity of the upper absorbent component 20.

The flexural rigidity of the bottom absorbent component 10 can be made higher than the flexural rigidity of the upper absorbent component 20 by making the weight (basis weight) of the material constituting the bottom absorbent component 10 greater than that of the upper absorbent component 20. Alternatively, even when the materials constituting the bottom absorbent component 10 and the upper absorbent component 20 have the same weight, the flexural resistance when flexed in the longitudinal direction can be increased by making the thickness of the bottom absorbent component 10 greater than the thickness of the upper absorbent component 20, and the flexural rigidity of the bottom absorbent component 10 can be made higher than the flexural rigidity of the upper absorbent component 20.

A difference in thickness can be provided by bringing the nonwoven cloth constituting the bottom absorbent component 10 into contact with a hot roller and heat-treating the nonwoven cloth, or by heat-treating with hot air and restoring the volume when at least one sheet selected from the surface sheet 11 and the middle sheet 12 of the bottom absorbent component 10 is a nonwoven cloth that includes synthetic resin fibers. Alternatively, the thickness of the bottom absorbent component 10 can be made greater than the thickness of the upper absorbent component 20 by creating corrugation so that at least one (the surface sheet 11 in FIG. 2A) of the sheets selected from the surface sheet 11 and middle sheet 12 of the bottom absorbent component 10 has a rippled shape as viewed in lateral cross-section, and is filled so that the tops and bottoms of the waves extend parallel to the longitudinal direction, as shown in FIG. 2B. As a result, the flexural rigidity of the bottom absorbent component 10 can be increased.

The corrugation can be applied by providing a pair of gear rolls in which a repeating pattern of depressions and protrusions is formed along the peripheral surface, and passing the nonwoven cloth between the gear rolls.

In the absorbent article 1 of the first embodiment shown in FIG. 1 and FIGS. 2A and 2B, the middle sheet 12 of the bottom absorbent component 10 and the middle sheet 22 of the upper absorbent component 20 are formed from nonwoven cloths having the same weight and fiber composition, and only the middle sheet 12 of the bottom absorbent component 10 is heat treated and allowed to restore its volume. As a result, the flexural rigidity of the bottom absorbent component 10 is made higher than the flexural rigidity of the upper absorbent component 20. The surface sheet 11 of the bottom absorbent component 10 and the surface sheet 21 of the upper absorbent component 20 are also nonwoven cloths having the same weight and fiber composition, and both sheets are corrugated.

As a method for making the flexural rigidity of the bottom absorbent component 10 greater than the flexural rigidity of the upper absorbent component 20, the article backing sheet 13 of the bottom absorbent component 10 may be formed from a material that has higher rigidity than the back surface sheet 23 of the upper absorbent component 20. For example, the back surface sheet 23 is formed from a resin film or nonwoven cloth, and the article backing sheet 13 is formed from a laminate of a nonwoven cloth and a resin film.

As previously mentioned, by heat-treating and restoring the volume of the nonwoven cloth constituting the bottom absorbent component 10, and/or applying corrugation to the nonwoven cloth constituting the bottom absorbent component 10, the compression recovery rate when the bottom absorbent component 10 is compressed in the thickness direction can be made higher than the compression recovery rate of the upper absorbent component 20.

The compression recovery rate can be measured using a "KES FB3-AUTO-A" automatic compression tester manufactured by Kato Tech Co. (Ltd.). A summary of the graph obtained in this measurement is shown in FIG. 11.

The bottom absorbent component 10 composed of the surface sheet 11, middle sheet 12, and article backing sheet 13, or the upper absorbent component 20 composed of the surface sheet 21, middle sheet 22, and back surface sheet 23 is separately placed in the automatic compression tester. An initial pressure P0 of 49 Pa (0.5 g/cm$^2$) is applied in the direction perpendicular to the sample by a circular pressing plate having a surface area of 2 cm$^2$, and the measured thickness at this time is designated as the initial thickness dimension T0. The compression pressure is linearly increased to Pm=4900 Pa (50 g/cm$^2$) at a compression rate of 50 seconds/1 mm with the initial pressure P0 as the starting point, and the pressed thickness of the measurement sample when the compression pressure Pm is applied is designated as Tm.

Figure 11:
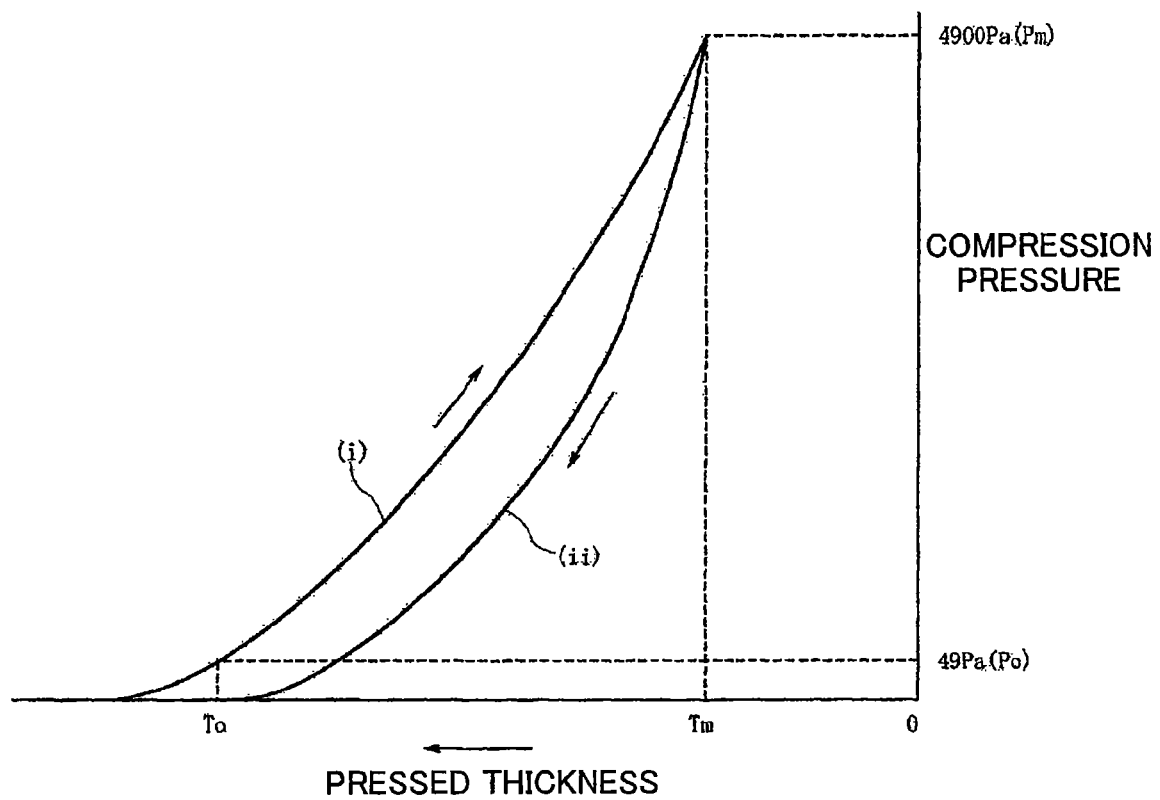
FIG. 11 is a diagram showing the compression recovery rate.

The work of compression WC (N·m/m$^2$) is the value obtained by integrating the equation WC=∫P·dT (wherein P is pressure and T is thickness) from T0 to Tm with respect to curve (i) in FIG. 11 obtained when the sample is compressed as described above. The work of compression recovery WC' is the value (N·m/m$^2$) obtained when integration is performed in the same manner as described above with respect to curve (ii) when the compression pressure is returned from Pm to P0. The compression recovery rate (RC value) is found by the equation WC'/WC×100(%).

The compression recovery rate (RC value) of the upper absorbent component 20 is preferably 40% or higher, and more preferably 50% or higher. The maximum is 100%.

Heat treatment need not necessarily be performed as described above when a plurality of sheets of bulky material having cushioning properties, such as through-air nonwoven cloth, are layered and used for the upper absorbent component 20 in order to give the upper absorbent component 20 a higher compression recovery rate than the bottom absorbent component 10.

When this absorbent article 1 is used, the release sheet provided on the clothing-facing surface of the article backing sheet 13 is peeled off, the article backing sheet 13 is adhesively fixed to the crotch portion of the undergarment via the pressure-sensitive adhesive layer, and the upper absorbent component 20 is placed against the vaginal opening or other discharge area. The upper absorbent component 20 absorbs vaginal discharge, blood, or other discharged liquid, and when the upper absorbent component 20 is contaminated, a finger is inserted between the surface sheet 11 of the bottom absorbent component 10 and the back surface sheet 23 of the upper absorbent component 20 in the excluded portion of the temporal adhesive member 8 having width dimension W1 shown in FIG. 1. The upper absorbent component 20 is then lifted up, the bond of the temporal adhesive member 8 is released, and the upper absorbent component 20 is separated from the bottom absorbent component 10. The surface sheet 11 of the bottom absorbent component 10 is then used after being placed against the discharge area.

As described above, by making the flexural rigidity of the bottom absorbent component 10 higher than the flexural rigidity of the upper absorbent component 20, deformation of the bottom absorbent component 10 can be reduced in comparison with the amount of deformation of the upper absorbent component 20 even when the upper absorbent component 20 is twisted or wrinkled by body movement or undergarment movement during use of the upper absorbent component 20 against the discharge area. It thereby becomes easy for the bottom absorbent component 10 to maintain a flat state when the upper absorbent component 20 is peeled off after absorbing and becoming contaminated with discharged material.

The bottom absorbent component 10 is heat treated and allowed to restore its volume. In addition to or in lieu of this treatment, corrugation is applied to the surface sheet 11 and other components, and a compression recovery rate of 40% or higher, more preferably 50% or higher, is obtained. The compression recovery rate of the bottom absorbent component 10 is higher than the compression recovery rate of the upper absorbent component 20. Therefore, the bottom absorbent component 10 is pressed into the upper absorbent component 20, and the overall thickness of the absorbent article 1 is not significantly increased when the bottom absorbent component 10 and the upper absorbent component 20 are layered together. When the contaminated upper absorbent component 20 is peeled off, the thickness of the bottom absorbent component 10 is restored, and when the bottom absorbent component 10 is used alone, the component feels soft against the discharge area. Adequate liquid-absorption capability can also be demonstrated by the bottom absorbent component 10 whose thickness is restored.

The temporal adhesive member 8 is formed in the area in which the surface sheet 11 and the middle sheet 12 are layered in the bottom absorbent component 10, and also in the area in which the surface sheet 21, middle sheet 22, and back surface sheet 23 are layered in the upper absorbent component 20. Therefore, when the upper absorbent component 20 is peeled off, the surface sheet 21, middle sheet 22, and back surface sheet 23 are lifted up together and separated from the bottom absorbent component 10, and the upper absorbent component 20 is easily peeled off. In the bottom absorbent component 10, the force with which the upper absorbent component 20 is peeled off in the area of the temporal adhesive member 8 can be compensated for by the triple-layer laminate composed of the surface sheet 11, middle sheet 12, and article backing sheet 13. Therefore, wrinkling and other adverse effects are unlikely to occur in the bottom absorbent component 10 even when the bottom absorbent component 10 is acted upon by this peeling force.

Figure 3:
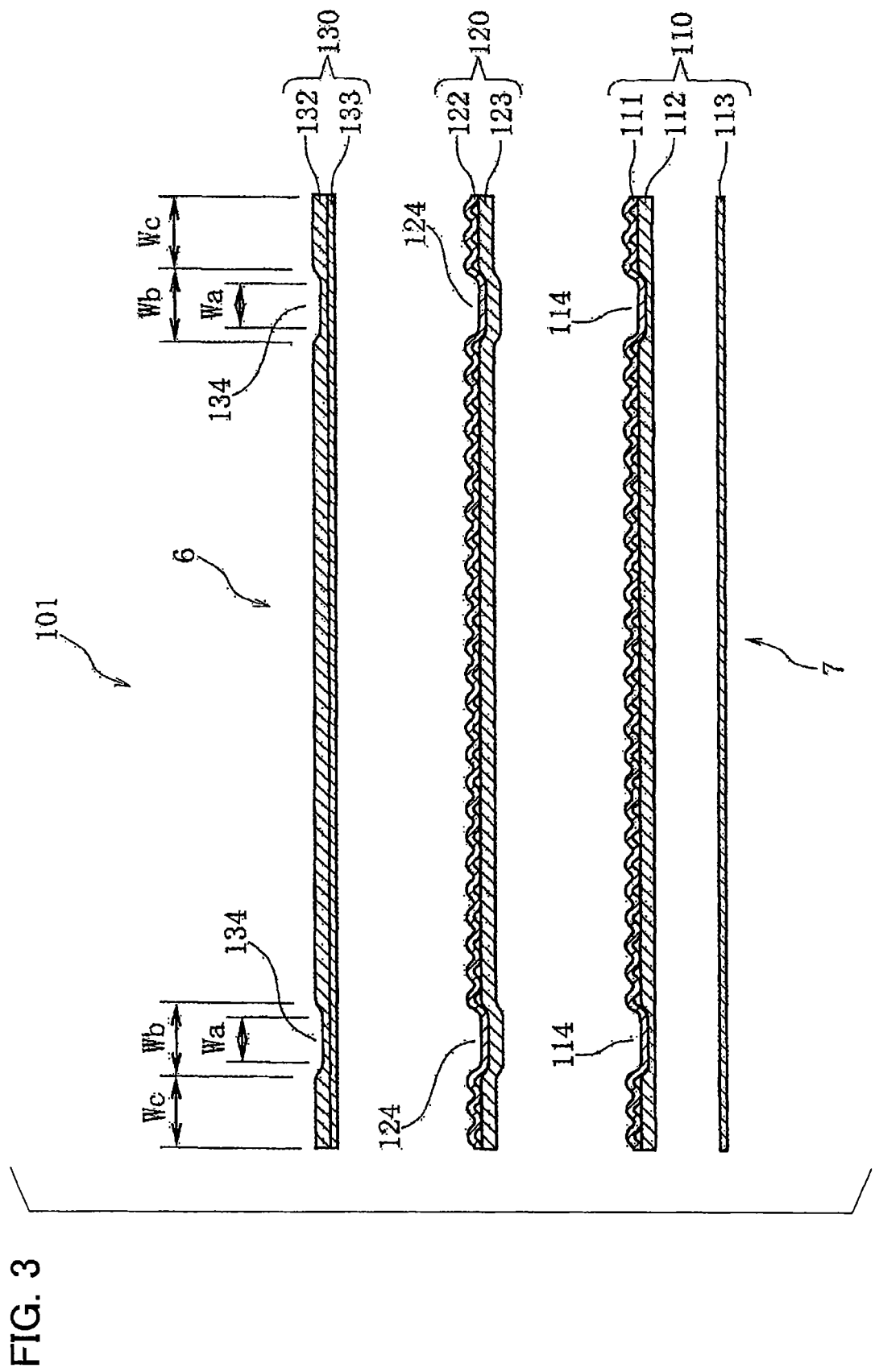
FIG. 3 is a separated sectional view showing each absorbent component of the absorbent article according to a second embodiment of the present invention.

FIG. 3 shows the absorbent article 101 according to a second embodiment of the present invention. The drawing is a separated sectional view showing a state in which each absorbent component is separated.

In this absorbent article 101, a bottom absorbent component 110 is provided on the clothing-facing surface 7, an upper absorbent component 120 is layered on the bottom absorbent component 110, and a top absorbent component 130 is furthermore provided on the skin-facing surface 6.

In the bottom absorbent component 110, a surface sheet 111 and a middle sheet 112 are layered and bonded together by a hot-melt adhesive applied in an amount that does not inhibit the transmission of liquid, and the surface sheet 111 and middle sheet 112 are also fixed in a round seal 114. In the upper absorbent component 120, a surface sheet is not provided, and a middle sheet 122 and a back surface sheet 123 are laminated together, bonded by a hot-melt adhesive, and fixed to each other by a round seal 124. In the top absorbent component 130, a middle sheet 132 and a back surface sheet 133 are bonded together by a hot-melt adhesive and fixed by a round seal 134.

In this embodiment, the upper absorbent component 120 has a two-layer structure that includes the middle sheet 122 and the back surface sheet 123. Therefore, the round seal 124 of the upper absorbent component 120 is not necessarily needed when the two layers are securely fixed with a hot-melt adhesive. This applies in the same manner to the top absorbent component 130, and the round seal 134 of the top absorbent component 130 is not necessarily needed.

The surface sheet 111 and middle sheet 112 of the bottom absorbent component 110, the upper absorbent component 120, and the top absorbent component 130 are layered together, and the bottom absorbent component 110, upper absorbent component 120, and top absorbent component 130 are temporarily fixed together in a separable manner by a temporal adhesive member 8 having the same pattern as the one shown in FIG. 1. After this temporary fixing, an article backing sheet 113 is bonded to the middle sheet 112 of the bottom absorbent component 110 by a hot-melt adhesive.

The pattern shape of the pressure portions in each of the round seals 114, 124, and 134 and the temporal adhesive member 8 is the same as in the first embodiment. The preferred ranges of the width dimension Wa of the round seals 114, 124, and 134, the width dimension Wb of the temporal adhesive member 8, the distance Wc from the edge to the temporal adhesive member 8 and round seal, and other dimensions are also the same as in the first embodiment.

The absorbent article 101 of this embodiment is used with the top absorbent component 130 placed against the discharge area. When the top absorbent component 130 is contaminated, the top absorbent component 130 is peeled off, and the upper absorbent component 120 is used after being placed against the discharge area. When the upper absorbent component 120 has also become contaminated, this upper absorbent component 120 is peeled off, and the bottom absorbent component 110 is used after being placed against the discharge area.

The flexural rigidity of the absorbent components in the longitudinal direction is higher in the bottom absorbent component 110 than in the top absorbent component 130. The flexural rigidity of the upper absorbent component 120 is higher than in the top absorbent component 130 and lower than in the bottom absorbent component 110. The compression recovery rate of the bottom absorbent component 110 when compressed in the thickness direction is higher than in the top absorbent component 130, and the compression recovery rate of the upper absorbent component 120 is higher than that of the top absorbent component 130 and lower than that of the bottom absorbent component 110.

In the embodiment shown in FIG. 3, the middle sheet 132 of the top absorbent component 130 and the middle sheet 122 of the upper absorbent component 120 are nonwoven cloths having the same weight and fiber composition. However, corrugation is applied to the middle sheet 122 of the upper absorbent component 120, the thickness of the upper absorbent component 120 is increased beyond the thickness of the top absorbent component 130, and flexural rigidity and compression recovery rate of the upper absorbent component 120 are both higher than in the top absorbent component 130. In the bottom absorbent component 110, the middle sheet 112 is heat-treated and allowed to restore its volume, the corrugation is applied to the surface sheet 111, the bottom absorbent component 110 is provided with the greatest thickness and weight, and the flexural rigidity and compression recovery rate are both set higher in the bottom absorbent component 110 than in the upper absorbent component 120 and top absorbent component 130.

It is preferred in the absorbent article 1 of the first embodiment that the bottom absorbent component 10 and the upper absorbent component 20 be visually distinguishable from each other. A configuration is also preferably adopted in the absorbent article 101 of the second embodiment wherein at least the bottom absorbent component 110 can be visually distinguished from the upper absorbent component 120 and the top absorbent component 130. Furthermore, it is preferred that the bottom absorbent component 110, the upper absorbent component 120, and the top absorbent component 130 be visually distinguishable from each other.

Causing each absorbent component to be a different color makes it possible to visually distinguish the absorbent components. For example, a configuration may be adopted whereby any of the absorbent components is formed from white fibers, and the skin-facing surface is made white, whereas another absorbent component is formed from colored fibers, and the skin-facing surface is a color other than white. For example, when a catechin as a functional agent that demonstrates deodorant capability is added to the middle sheets 12 and 112 and/or the surface sheets 11 and 111 constituting the bottom absorbent component 10 or 110, a green colorant is also preferably used that suggests the presence of the catechin. The skin-facing surface of the bottom absorbent components 10 and 110 thereby shows a pale green color. When the upper absorbent component or top absorbent component is composed of white fibers in this instance, it is easy to visually distinguish during use whether the bottom absorbent components 10 and 110 are in use. When a catechin has been added, antimicrobial effects and deodorant effects can be demonstrated by the bottom absorbent components 10 and 110 that are worn for the longest time, and unpleasant odor can be prevented even when the article is worn for a long period of time. It is also possible to add the catechin to the upper absorbent components 20 and 120 or the top absorbent component 130.

Figure 6A:
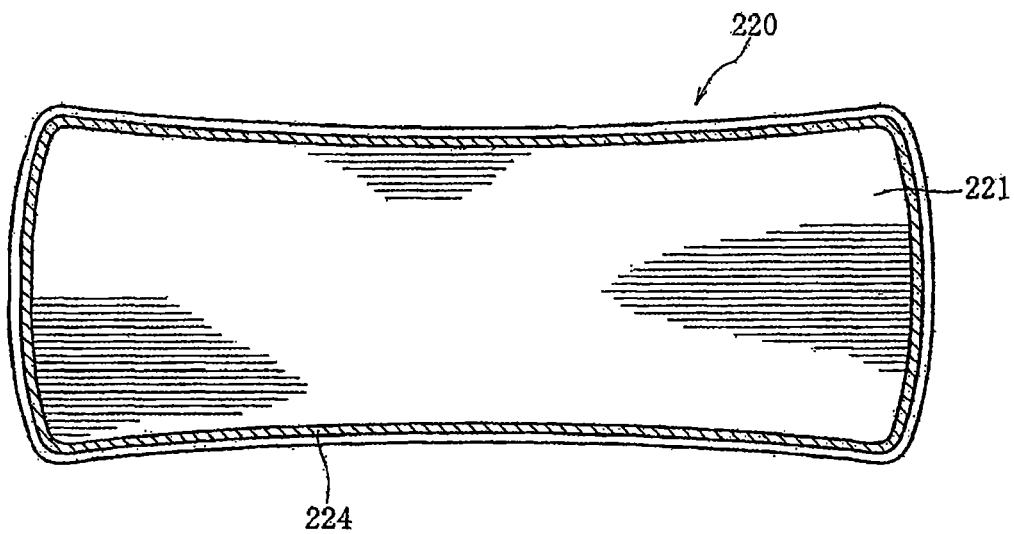
FIG. 6A is a plan view of the upper absorbent component as viewed from the skin-facing surface.
Figure 6B:
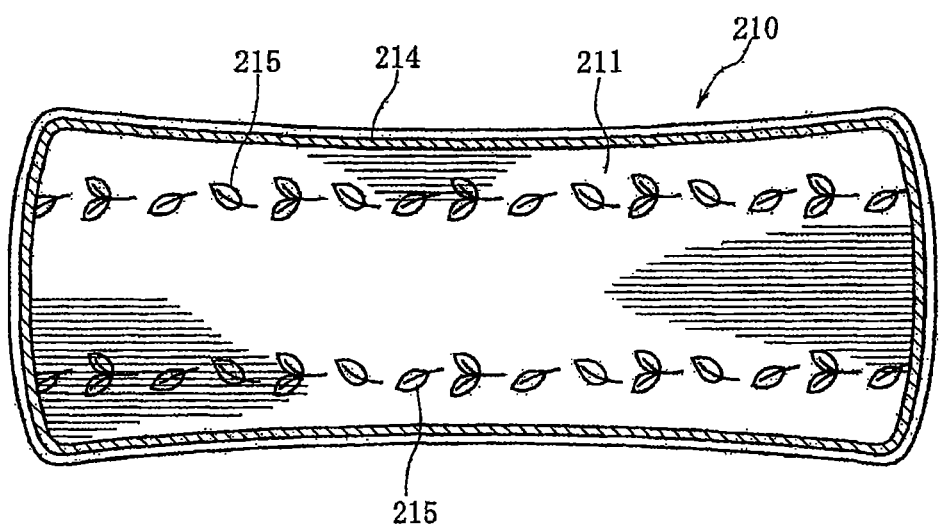
FIG. 6B is a plan view of only the bottom absorbent component as viewed from the skin-facing surface.

FIGS. 6A and 6B are plan views showing a third embodiment in which the absorbent components are visually distinguishable from each other. FIG. 6A is a plan view of the upper absorbent component 220 as viewed from the skin-facing surface. FIG. 6B is a plan view of only the bottom absorbent component 210 as viewed from the skin-facing surface.

In the upper absorbent component 220 shown in FIG. 6A, a round seal 224 is formed in the periphery, and corrugation is applied to the surface sheet 221. This corrugation gives the cross-section of the surface sheet 221 a rippled shape, and the tops and bottoms of the waves extend linearly and in parallel fashion in the longitudinal direction. In the bottom absorbent component 210 shown in FIG. 6B, the same corrugation as previously described is applied to the surface sheet 211, and embossed portions 215 in a leaf design are furthermore formed in the surface sheet 211. Providing mutually different embossed patterns to the skin-facing surfaces of the bottom absorbent component 210 and the upper absorbent component 220 thereby makes it possible to easily distinguish visually between the bottom absorbent component 210 and the upper absorbent component 220.

When a configuration is adopted in which corrugation is applied to the surface sheet of the bottom absorbent component, and corrugation is not applied to the surface sheet of the upper absorbent component, the bottom absorbent component can easily be distinguished visually from the upper absorbent component by visually determining whether corrugation is present. By applying corrugation to the surface sheet of the bottom absorbent component as described above, the bottom absorbent component can be endowed with a higher flexural rigidity and compression recovery rate than the upper absorbent component.

As described above, visual distinction of the absorbent components is made possible by using different material in the surface sheets of the bottom absorbent component and the upper absorbent component, or by varying the structure of the surface sheets.

By making it possible to distinguish between the bottom absorbent component and the upper absorbent component as viewed from the skin-facing surfaces thereof, the absorbent component that is currently in contact with the discharge area can be identified, the user can be prevented from being inconvenienced by mistakenly discarding the entire absorbent article when the upper absorbent component is in use, mistakenly removing the absorbent article from the undergarment without having a replacement absorbent article ready when the bottom absorbent component is in use, or experiencing other inconveniences.

Figure 7A:
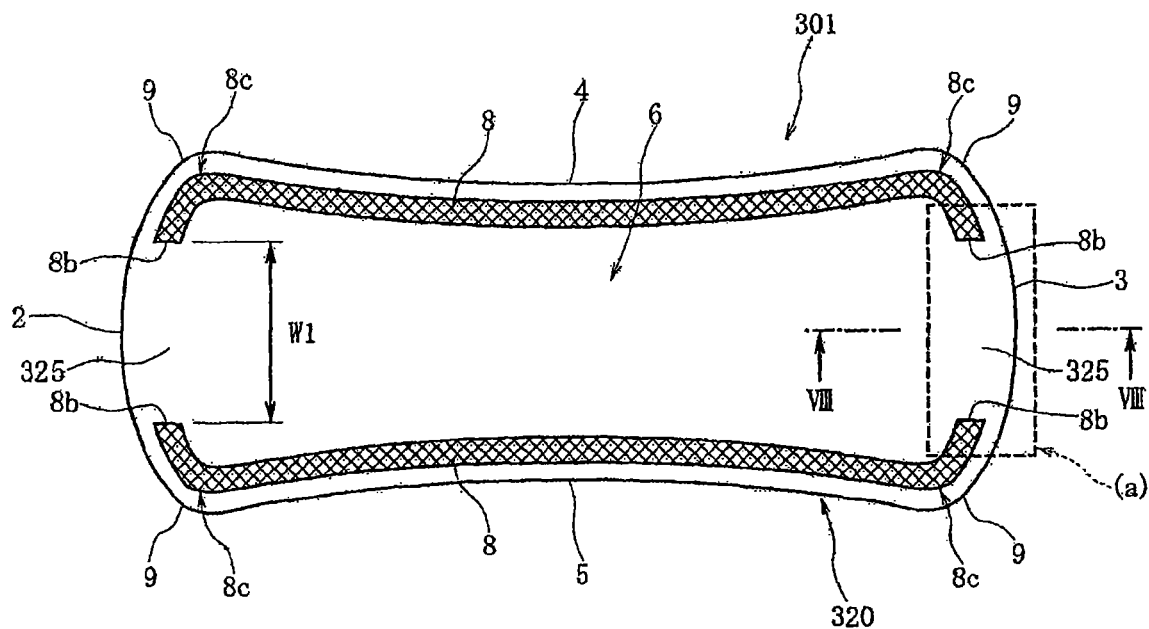
FIG. 7A is a plan view of the absorbent article according to a fourth embodiment of the present invention.
Figure 7B:
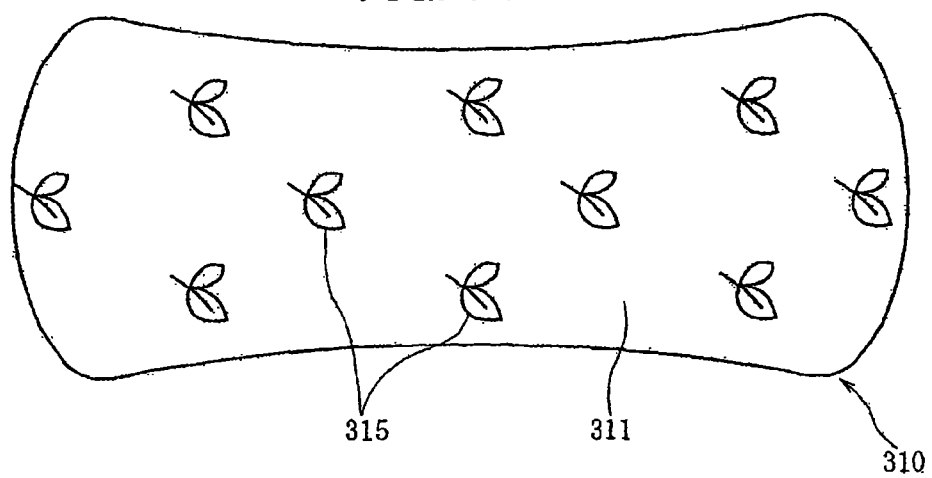
FIG. 7B is a plan view of a state in which the upper absorbent component is removed.
Figure 8:
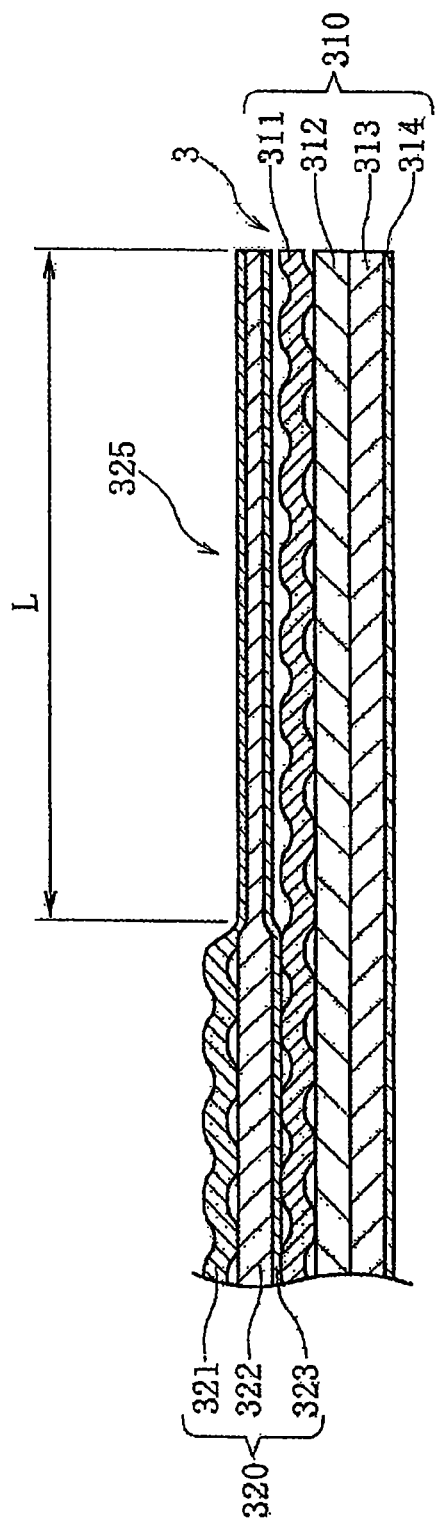
FIG. 8 is a partial sectional view along line VIII-VIII of FIG. 7A.
Figure 9:
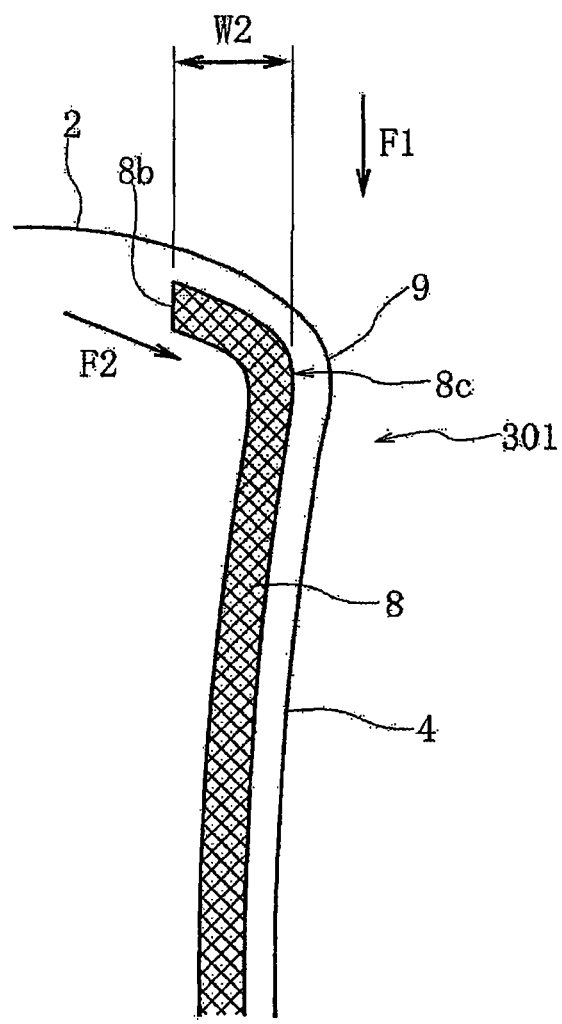
FIG. 9 is a partial plan view of the temporal adhesive member.

FIG. 7A is a plan view of the absorbent article 301 according to a fourth embodiment of the present invention as viewed from the skin-facing surface 6. FIG. 7B is a plan view of a state in which the upper absorbent component 320 is removed from the absorbent article 301, and specifically shows the bottom absorbent component 310 from the skin side. FIG. 8 is a partial sectional view along line VIII-VIII in FIG. 7A. FIG. 9 is a partial enlarged plan view showing the shape of the temporal adhesive member 8.

As shown in the partial sectional view in FIG. 8, this absorbent article 301 is formed from two layers that include the bottom absorbent component 310 and the upper absorbent component 320.

The bottom absorbent component 310 is formed from a surface sheet 311, a first middle sheet 312, a second middle sheet 313, and an article backing sheet 314. The surface sheet 311 is liquid-permeable, and the first middle sheet 312 and second middle sheet 313 are capable of absorbing and retaining liquid. In an alternative configuration, one of the first middle sheet 312 and second middle sheet 313 is liquid-absorbent, and the other sheet may have high bulk and low density and demonstrate cushioning ability. The article backing sheet 314 is air-permeable and liquid-impermeable.

A round seal is not formed in the bottom absorbent component 310, and the layers are bonded by a hot-melt adhesive. A rubber-based hot-melt adhesive is applied in a spiral pattern an amount of about 10 g/m$^2$ between the surface sheet 311 and the first middle sheet 312, and between the first middle sheet 312 and the second middle sheet 313 so that the layers can be securely bonded together without inhibiting the transmission of liquid. The second middle sheet 313 and the article backing sheet 314 are also securely fixed together by a hot-melt adhesive.

The abovementioned absorbent component 320 has a surface sheet 321, a middle sheet 322, and a back surface sheet 323. The surface sheet 321 is liquid-permeable, the middle sheet 322 is capable of absorbing and retaining liquid, and the back surface sheet 323 is air-permeable and liquid-impermeable.

A round seal is also not formed in the upper absorbent component 320, the surface sheet 321 and middle sheet 322 are securely fixed together by a hot-melt adhesive applied in an amount that does not inhibit the transmission of liquid, and the middle sheet 322 and back surface sheet 323 are also securely fixed together by a hot-melt adhesive.

As shown in FIG. 7A, the bottom absorbent component 310 and the upper absorbent component 320 are temporarily fixed together by the temporal adhesive member 8 so as to be able to separate. The pattern of the temporal adhesive member 8 is the same as in the first embodiment shown in FIG. 1, and the pattern of the pressure portions 8a of the temporal adhesive member 8, the preferred range of the width dimensions Wb of the temporal adhesive member 8, and other characteristics are the same as in the first embodiment. The strength of the bond between the bottom absorbent component 310 and the upper absorbent component 320 created by the temporal adhesive member 8 is set so as to be lower than the adhesion strength between the layers in the bottom absorbent component 310 and the adhesion strength between the layers of the upper absorbent component 320.

As shown in FIG. 7A, the temporal adhesive member 8 extends along the entire length of the edges that include the right-side edge 4 and left-side edge 5 of the absorbent article 301, and the ends 8b of the temporal adhesive member 8 are positioned inside the front edge 2 and the back edge 3. The space between the aforementioned ends 8b is an excluded portion in which the temporal adhesive member 8 is cut out towards the insides of the front edge 2 and back edge 3. The width dimension of this excluded portion is W1, and the preferred range thereof is the same as in the aforementioned first embodiment.

As shown in FIG. 7A, in the front edge 2 and the back edge 3, a compressed portion 325 in which the upper absorbent component 320 is partially compressed is formed in the area (a) that includes the excluded portion of the temporal adhesive member 8 and part of the temporal adhesive member 8. As shown in FIG. 8, the surface sheet 321, middle sheet 322, and back surface sheet 323 are all compressed at the compressed portion 325, and part of the upper absorbent component 320 is made thin. The compressed portion 325 is formed in an area that extends over a length L in the longitudinal direction from the front edge 2 and back edge 3. Length L is not particularly limited and may be about 5 mm to 30 mm, for example. The sum (2×L) of the lengths L of the compressed portions 325 formed in the front edge 2 and back edge 3 is preferably ¼ or less of the length dimension in the longitudinal direction of the absorbent article 301, and more preferably ⅕ or less thereof. Specifically, the compressed portions 325 do not extend to the central region of the absorbent article 301.

The compressed portion 325 is formed after the surface sheet 321, middle sheet 322, and back surface sheet 323 constituting the upper absorbent component 320 are bonded by the hot-melt adhesive, in a step that precedes the temporary fixing of the bottom absorbent component 310 and the upper absorbent component 320 by the temporal adhesive member 8. The compressed portion 325 is formed by pressing the upper absorbent component 320 at a normal or elevated temperature using a roll having a smooth surface or a roll on which a fine embossed pattern is formed on the surface.

When the compressed portion 325 is formed in the excluded portion, the surface sheet 321, middle sheet 322, and back surface sheet 323 constituting the upper absorbent component 320 become difficult to separate even when the temporal adhesive member 8 is not present, and it becomes possible to prevent layer separation from occurring in the upper absorbent component 320 in the excluded portion in which the temporal adhesive member 8 is not formed.

As shown in FIG. 8, a gap is easily formed in the excluded portion of the temporal adhesive member 8 between the bottom surface of the compressed portion 325 of the upper absorbent component 320 and the surface sheet 311 of the bottom absorbent component 310. It therefore becomes easy to grasp and peel off the upper absorbent component 320 by the fingers and in the excluded portion of the temporal adhesive member 8 when the upper absorbent component 320 has become contaminated.

As shown in FIG. 7A, the ends 8b of the temporal adhesive member 8 are positioned towards the inside with respect to the front edge 2 and back edge 3. As a result, a portion of the temporal adhesive member 8 is disposed at the corners 9 of the absorbent article 301; specifically, at the boundary between the right-side edge 4 and the front edge 2, the boundary between the right-side edge 4 and the back edge 3, the boundary between the left-side edge 5 and the front edge 2, and the boundary between the left-side edge 5 and the back edge 3. By having a portion of the temporal adhesive member 8 present at each corner 9, it becomes easy to prevent the upper absorbent component 320 from improperly separating from the bottom absorbent component 310 in the corners 9 when the absorbent article 301 is in use.

Inside the corners 9 of the absorbent article 301, portions of the temporal adhesive member 8 form outwardly convex curves 8c that follow the shape of the corners 9. The temporal adhesive member 8 has the curves 8c, and the ends 8b are disposed inside the front edge 2 and back edge 3. Therefore, the temporal adhesive member 8 is disposed in an area that extends over a width dimension W2 in the transverse direction in the front edge 2 and back edge 3, as shown in FIG. 9. The aforementioned W2 is preferably at least twice the width dimension Wb of the temporal adhesive member 8, and is more preferably at least three times the width dimension Wb.

When this absorbent article 301 is worn while fixed to the inside surface of an undergarment, and a longitudinally directed peeling force F1 shown in FIG. 9 is applied to the front edge 2 or back edge 3 in the excluded portion of the temporal adhesive member 8, the peeling force F1 can be received in the area that extends over the width dimension W2 because the temporal adhesive member 8 is present in the area that extends over the width dimension W2 in the front edge 2 and back edge 3. It is therefore easy to prevent the upper absorbent component 320 from being improperly separated from the bottom absorbent component 310 by the aforementioned peeling force F1.

When the upper absorbent component 320 is contaminated with vaginal discharge, blood, or the like, a lifting force acts in the forward direction with respect to the plane of paper in FIG. 9 on the upper absorbent component 320 at the front edge 2 or back edge 3 when the upper absorbent component 320 is grasped in the fingers and peeled off at the excluded portion of the temporal adhesive member 8 in the front edge 2 or back edge 3. As a result, a force F2 can be applied in the direction of the pattern of the temporal adhesive member 8 to the ends 8b of the temporal adhesive member 8, as shown in FIG. 9. The peeling force is thus propagated from the ends 8b along the curves 8c with respect to the temporal adhesive member 8, and it becomes possible to peel the upper absorbent component 320 from the bottom absorbent component 310 without imparting excessive resistance to the fingers.

The compressed portion 325 may also be applied in the other embodiments described previously, and the advantage of having curves 8c formed in the temporal adhesive member 8 is the same in the other embodiments.

As shown in FIG. 8, the surface sheet 311 of the bottom absorbent component 310 and the surface sheet 321 of the upper absorbent component 320 are both corrugated and have a rippled pattern formed therein. In this absorbent article 301, the bottom absorbent component 310 has a four-layer structure, and the upper absorbent component 320 has a three-layer structure. Therefore, the compression recovery rate and the flexural rigidity in the longitudinal direction can be made higher in the bottom absorbent component 310 than in the upper absorbent component 320.

As shown in FIG. 7B, embossed portions 315 formed in a leaf design are interspersed in the surface sheet 311 of the bottom absorbent component 310, and the bottom absorbent component 310 and upper absorbent component 320 are easy to visually distinguish from each other.

Figure 10:
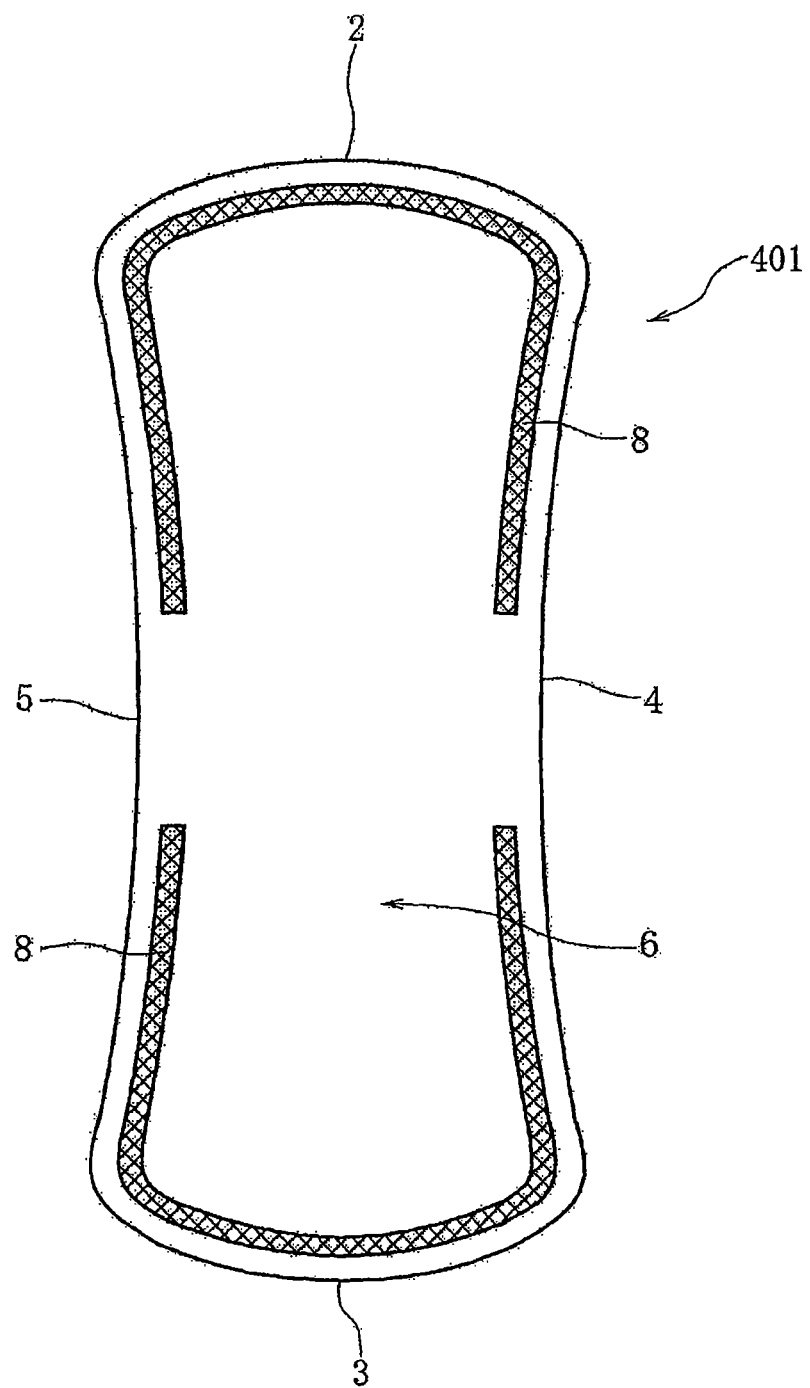
FIG. 10 is a plan view of the absorbent article according to a fifth embodiment of the present invention.

FIG. 10 is a plan view of the absorbent article 401 according to a fifth embodiment of the present invention as viewed from the skin-facing surface 6.

In this absorbent article 401, at least one upper absorbent component is layered on the bottom absorbent component in the same manner as in the embodiments described above. A plurality of layers is layered in each of the bottom absorbent component and the upper absorbent component, the layers are bonded together by a hot-melt adhesive in each of the absorbent components, and round seals are formed as needed in the absorbent components.

The bottom absorbent component and the upper absorbent component are temporarily fixed together by a temporal adhesive member 8. In the absorbent article 401 shown in FIG. 10, the temporal adhesive member 8 is formed along the entire length towards the inside of the front edge 2 and back edge 3, and excluded portions in which the temporal adhesive member 8 is interrupted are formed towards the inside of the right-side edge 4 and the inside of the left-side edge 5.

In the aforementioned embodiments, the catechin or other deodorant functional agent described above, or an antimicrobial agent, a fragrance, or the like is preferably included in at least the bottom absorbent components 10, 110, 210, and 310. However, the functional agent may also be included in each of the upper absorbent components 20, 120, 220, and 320, or the top absorbent component 130.

One or more types selected from phenols extracted from plants, such as catechins and the like, or active carbon, copper ions, silver ions, and the like may be used as the functional agent. As previously mentioned, a colorant is preferably used to impart a green color to the skin-facing surface of the absorbent component when a catechin is included, and when active carbon is used, a colorant that gives the skin-facing surface a black color is preferably used. The bottom absorbent component can easily be distinguished from the upper absorbent component by combining a colored absorbent component that includes these functional agents and colorants with a white-colored absorbent component, the bottom absorbent component can easily be distinguished visually from the upper absorbent component, as described above. By forming the embossed portions 215 and 315 in the leaf pattern shown in FIG. 6B or FIG. 7B in the skin-facing surface of the absorbent component to which a catechin is added, the absorbent component can be visually recognized as having antimicrobial and deodorant effects, and a fresh feeling can be imparted to the user.

Catechins are tea-leaf extracts extracted from tea leaves with water or hot water, and are included among the fibers of the middle sheet or surface sheet in the form of microparticles, attached to a microparticulate porous substance, or sealed inside microcapsules.

Catechins included in tea-leaf extracts include epicatechin, epicatechin gallate, epigallocatechin, epigallocatechin gallate, catechin gallate, and gallocatechin gallate. When a tea-leaf extract is used, 10% mass or more, and more preferably 30% mass or more, of epigallocatechin gallate is preferably included in the tea-leaf extract.

Copper phthalocyanine green and other phthalocyanine-based colorants can be used. It is also possible to use a copper chlorophyll-based colorant, which is a natural food colorant. The hue of the colorant preferably demonstrates concealing effects with respect to vaginal discharge (colorless to light brown) and urine (light yellow) among bodily fluids. In order to enhance the impression of a catechin as a naturally occurring tea extract, a hue between 10 YR and 10 G according to the Munsell color system is desired for this coloration with consideration for the green color of tea leaves. A hue from 10 Y to 10 G is preferred.

Tea-leaf extract is included in the middle sheet, for example, and is added in a range of 0.1 to 1.0% mass with respect to the mass of the middle sheet. The aforementioned colorant is added in the range of 10 to 30 mass parts with respect to 100 mass parts of the tea-leaf extract. When the tea-leaf extract is used in the form of microparticles, the size of the microparticles is preferably 5 micrometers or less, and more preferably 2 micrometers or less.

(1) Example 1

An absorbent article 1 having a two-layer structure that included a bottom absorbent component 10 and an upper absorbent component 20 was created as shown in FIGS. 2A and 2B.

The surface sheet 11 of the bottom absorbent component 10 and the surface sheet 21 of the upper absorbent component 20 were both formed from spunlace nonwoven cloth composed of 60% mass of rayon fibers and 40% mass of polyethylene terephthalate fibers. The weight thereof was 35 g/m$^2$. Corrugation was applied to the surface sheet 11 and the surface sheet 21.

The middle sheet 12 of the bottom absorbent component 10 and the middle sheet 22 of the upper absorbent component 20 were both formed from through-air nonwoven cloth composed of 50% mass of polyethylene fibers and 50% mass of polypropylene fibers. The polyethylene fibers and polypropylene fibers used both had a fineness of 2.2 dtex and a fiber length of 40 mm, and the weight thereof was 25 g/m$^2$. The through-air nonwoven cloth constituting the middle sheet 12 of the bottom absorbent component 10 was brought into contact with two hot rollers in an S-shape at 120 degrees C., heat-treated, and allowed to restore its volume.

The thickness of the heat-treated middle sheet 12 was 1.4 mm, and the thickness of the non-heat-treated middle sheet 22 of the upper absorbent component 20 was 0.5 mm. The compression recovery rate (RC value) of the heat-treated middle sheet 12 when measured alone was 53.83%.

The article backing sheet 13 of the bottom absorbent component 10 and the back surface sheet 23 of the upper absorbent component 20 were both formed from air-permeable polyethylene film having a basis weight of 35 g/m$^2$.

As shown in FIG. 1 and FIGS. 2A and 2B, a round seal 14 was formed in the bottom absorbent component 10, a round seal 24 was formed in the upper absorbent component 20, and a temporal adhesive member 8 was formed for the temporary fixing of the bottom absorbent component 10 to the upper absorbent component 20.

The bottom absorbent component 10 and the upper absorbent component 20 were formed from the same material, but by heat-treating and restoring the volume of the middle sheet 12 of the bottom absorbent component 10, the thickness of the bottom absorbent component 10 was made greater than that of the upper absorbent component 20, and it became possible to make the flexural rigidity and compression recovery rate greater in the bottom absorbent component 10 than in the upper absorbent component 20.

(2) Example 2

An absorbent article having a two-layer structure was created in the same manner as in Example 1.

The surface sheet 11, middle sheet 12, and article backing sheet 13 of the bottom absorbent component 10 were the same as those used in Example 1.

The surface sheet 21 of the upper absorbent component 20 was formed from through-air nonwoven cloth composed of 50% mass of polyethylene fibers and 50% mass or polypropylene fibers. The polyethylene fibers and polypropylene fibers that were used both had a fineness of 2.2 dtex and a fiber length of 40 mm, and the weight thereof was 25 g/m$^2$. The nonwoven cloth that was used was neither heat-treated for volume recovery nor corrugated.

An air-laid nonwoven cloth in which pulp was laminated by an air-laying method and the fibers were bonded together by a binder was used as the middle sheet 22 of the upper absorbent component 20. The weight thereof was 35 g/m$^2$. The back surface sheet 23 of the upper absorbent component 20 was an SMS composite nonwoven cloth having a weight of 20 g/m$^2$.

As shown in FIG. 1 and FIGS. 2A and 2B, a round seal 14 was formed in the bottom absorbent component 10, a round seal 24 was formed in the upper absorbent component 20, and a temporal adhesive member 8 was formed for temporarily fixing the bottom absorbent component 10 to the upper absorbent component 20.

By making the total weight (basis weight) of the materials constituting the bottom absorbent component 10 greater than that of the upper absorbent component 20, the flexural rigidity of the bottom absorbent component 10 was set higher than that of the upper absorbent component 20. The middle sheet 12 used in the bottom absorbent component 10 had its volume restored by heat treatment, and the bottom absorbent component 10 had a higher compression recovery rate than the upper absorbent component 20.

(3) Example 3

An absorbent article 101 having the three-layer structure shown in FIG. 3 was created as in Example 3.

The surface sheet 111 and middle sheet 112 of the bottom absorbent component 110 were the same as the surface sheet 11 and middle sheet 12 used in Example 1. A laminate of SMS composite nonwoven cloth having a weight of 20 g/m$^2$ and an air-permeable polyethylene film having a basis weight of 20 g/m$^2$ were used as the article backing sheet 113.

A corrugated spunlace nonwoven cloth composed of 60% mass of cotton fibers and 40% mass of polyethylene terephthalate fibers was used as the middle sheet 122 of the upper absorbent component 120. An air-permeable polyethylene film having a basis weight of 35 g/m$^2$ was used as the back surface sheet 123.

A non-corrugated spunlace nonwoven cloth having a weight of 35 g/m$^2$ composed solely of cotton fibers was used as the middle sheet 132 of the top absorbent component 130. An air-permeable polyethylene film having a basis weight of 23 g/m$^2$ was used as the back surface sheet 133.

As shown in FIG. 3, a round seal 114 was formed in the bottom absorbent component 110, and a round seal 124 was formed in the upper absorbent component 120. A round seal 134 was formed in the top absorbent component 130. A temporal adhesive member 8 was formed for temporarily fixing together the bottom absorbent component 110, upper absorbent component 120, and top absorbent component 130.

By setting the weight and basis weight so as to increase in sequence from the top absorbent component 130 to the upper absorbent component 120 to the bottom absorbent component 110, the flexural rigidity was also set so as to increase in the same sequence. The middle sheet 122 of the upper absorbent component 120 was also corrugated, and the thickness thereof was increased, whereby the flexural rigidity and compression recovery rate were increased. In the bottom absorbent component 110, the middle sheet 112 was heat-treated and allowed to recover its volume, and the surface sheet 111 was corrugated and increased in thickness, whereby the flexural rigidity was increased, and the compression recovery rate was also increased.

(4) Example 4

As shown in FIGS. 7 through 9, an absorbent article was created without round seals formed in the absorbent components.

The bottom absorbent component 310 had a four-layer structure, the same as shown in FIG. 8. The surface sheet 311 was a spunlace nonwoven cloth composed of 60% mass of rayon fibers and 40% mass of polyethylene terephthalate fibers, and the weight thereof was 35 g/m$^2$. A corrugated sheet was used as the surface sheet 311. The first middle sheet 312 was a spunlace nonwoven cloth composed of 90% mass of rayon fibers and 10% mass of hydrophilized polypropylene fibers, and the weight thereof was 30 g/m$^2$. The second middle sheet 313 was a through-air nonwoven cloth composed of 50% mass of hydrophilized polyethylene fibers and 50% mass of hydrophilized polypropylene fibers, and the weight thereof was 30 g/m$^2$. The article backing sheet 314 was formed from an air-permeable polyethylene film having a basis weight of 35 g/m$^2$.

The upper absorbent component 320 had a three-layer structure that included a surface sheet 321, a middle sheet 322, and a back surface sheet 323; the surface sheet 321 was the same as the surface sheet 311 of the bottom absorbent component 310; and the middle sheet 322 and back surface sheet 323 were the same as the first middle sheet 312 and article backing sheet 314 of the bottom absorbent component 310. Specifically, the upper absorbent component 320 had the same structure as the bottom absorbent component 310 without the second middle sheet 313. In the bottom absorbent component 310, the surface sheet 311 was layered with the first middle sheet 312, and embossed portions 315 were formed in the leaf design shown in FIG. 7B.

The bottom absorbent component 310 and upper absorbent component 320 were layered together, and a temporal adhesive member 8 was formed.

In Example 4, the bottom absorbent component 310 had a four-layer structure, and the upper absorbent component 320 had a three-layer structure. Therefore, the flexural rigidity of the bottom absorbent component 310 could be set higher than that of the upper absorbent component 320. The compression recovery rate could also be set higher in the bottom absorbent component 310 than in the upper absorbent component 320.

Tea-leaf extract and green colorant were added to the first middle sheet 312 of the bottom absorbent component 310 and the middle sheet 322 of the upper absorbent component 320, the green color was visible through the surface sheet 311 in the bottom absorbent component 310, and the green color was visible through the surface sheet 321 in the upper absorbent component 320.

The component ratios of catechins included in the tea-leaf extract were 31.5% mass of epigallocatechin gallate, 17.2% mass of epigallocatechin, 17.2% mass of gallocatechin, 5.9% mass of epicatechin, 5.0% mass of epicatechin gallate, 2.8% mass of catechin gallate, and 1.9% mass of gallocatechin gallate. The tea leaf powder including these catechins was used in the form of microparticles having a diameter of less than 2 micrometers. The tea leaf powder was added in the amount of 0.38% mass with respect to the masses of the first middle sheet 312 and the middle sheet 322.

Copper phthalocyanine green having a green color was used as the colorant. The colorant was added in the amount of 15% mass per 100% mass of the tea-leaf extract included in each of the first middle sheet 312 and the middle sheet 322.

The first middle sheet 312 and middle sheet 322 were manufactured according to a method whereby rayon fibers and polypropylene fibers were mixed in a mass ratio of 90:10, respectively; a spunlace nonwoven cloth having a weight of 30 g/m² was formed; this spunlace nonwoven cloth was placed in a drum-type dyeing machine; a nonionic/anionic surfactant as a dispersing agent was added and the product was stirred; tea-leaf extract and copper phthalocyanine green were added; the tea-leaf extract was fixed to the fibers; and the fibers were colored green.

(5) Example 5

An absorbent article was manufactured in which the bottom absorbent component had a three-layer structure, the upper absorbent component had a two-layer structure, the skin-facing surface of the upper absorbent component was white, and the skin-facing surface of the bottom absorbent component was green.

In the bottom absorbent component, the surface sheet was the same as the first middle sheet 312 of Example 4; specifically, the surface sheet was formed from a spunlace non-woven cloth that included tea-leaf extract and a green colorant. A non-corrugated sheet was used. The middle sheet and article backing sheet used in the bottom absorbent component were the same as the heat-treated and re-voluminized middle sheet 12 and article back surface sheet 13 used in the bottom absorbent component of Example 1.

The surface sheet of the upper absorbent component was a through-air nonwoven cloth having a weight of 25 g/m² formed from 50% mass of hydrophilized polyethylene fibers and 50% mass of hydrophilized polypropylene fibers, and the back surface sheet was an SMS composite nonwoven cloth having a weight of 20 g/m².

The bottom absorbent component and upper absorbent component used were not provided with round seals, and the layers thereof were bonded together. The bottom absorbent component and the upper absorbent component were layered together, and a temporal adhesive member 8 was formed.

It was possible to set a higher flexural rigidity and compression recovery rate in the bottom absorbent component than in the upper absorbent component.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article comprising:
a bottom absorbent component which is one of a plurality of layered absorbent components having a liquid-absorbent layer, and which is positioned in a bottom stage having a clothing-facing surface provided with positioning-fixing means fixed to a piece of clothing, and having a skin-facing surface on the opposite side from the clothing-facing surface; and
an upper absorbent component which is one of the plurality of layered absorbent components, and which is peelably bonded to the skin-facing surface of the bottom absorbent component;
wherein the bottom absorbent component has higher flexural rigidity than the upper absorbent component when flexed in the longitudinal direction, which is the antero-posterior direction between the legs during fitting to the body,
wherein the skin-facing surface of the bottom absorbent component and a skin-facing surface of the upper absorbent component differ in color from each other,
wherein each of the plurality of layered absorbent components is of substantially the same width, and
wherein each of the bottom and upper absorbent components has a center portion and an end portion in the longitudinal direction, and the upper absorbent component's center portion and end portion are different in thickness from each other, and the bottom absorbent component's center portion and end portion are of substantially the same thickness.

2. The absorbent article according to claim 1, wherein a plurality of the upper absorbent components is provided, each upper absorbent component is peelably layered, and the flexural rigidity is higher in the bottom absorbent component than in the upper absorbent component disposed at the top.

3. The absorbent article according to claim 1, wherein a plurality of the upper absorbent components is provided, each upper absorbent component is peelably layered, and the flexural rigidity is higher in any of the plurality of upper absorbent components that is positioned closer to the clothing than in any of the plurality of upper absorbent components that is positioned closer to the skin.

4. The absorbent article according to claim 1, wherein the flexural rigidity of the bottom absorbent component is increased by making the weight of the material constituting the bottom absorbent component greater than that of the upper absorbent component.

5. The absorbent article according to claim 1, wherein the flexural rigidity of the bottom absorbent component is increased by making the thickness of the bottom absorbent component greater than that of the upper absorbent component.

6. The absorbent article according to claim 5, wherein the bottom absorbent component comprises nonwoven cloth, and the nonwoven cloth is heat-treated and increased in thickness.

7. The absorbent article according to claim 5, wherein the thickness is increased by forming irregularities in the surface layer of the bottom absorbent component.

8. An absorbent article comprising:
a bottom absorbent component which is one of a plurality of layered absorbent components having a liquid-absorbent layer, and which is positioned in a bottom stage having a clothing-facing surface provided with positioning-fixing means fixed to a piece of clothing, and having a skin-facing surface on the opposite side from the clothing-facing surface; and
an upper absorbent component which is one of the plurality of layered absorbent components, and which is peelably bonded to the skin-facing surface of the bottom absorbent component;
wherein the compression recovery rate (RC value) of the bottom absorbent component in a thickness direction is higher than that of the upper absorbent component,
wherein each of the plurality of layered absorbent components is of substantially the same width, and
wherein each of the bottom and upper absorbent component has a center portion and an end portion in the longitudinal direction, and the upper absorbent component's center portion and end portion are different in thickness from each other, and the bottom absorbent component's center portion and end portion are of substantially the same thickness.

9. The absorbent article according to claim 8, wherein a plurality of the upper absorbent components is provided, each upper absorbent component is peelably layered, and the bottom absorbent component has a higher compression recovery rate (RC value) than does the uppermost of the plurality of the upper absorbent components.

10. The absorbent article according to claim 8, wherein a plurality of the upper absorbent components is provided, each upper absorbent component is peelably layered, and any of the plurality of upper absorbent components that is positioned closer to the clothing has a higher compression recovery rate (RC value) than any of the upper absorbent components that is positioned closer to the skin.

11. The absorbent article according to claim 8, wherein the compression recovery rate (RC value) of at least one of the materials constituting the bottom absorbent component is 40% or higher.

12. An absorbent article comprising:
a bottom absorbent component which is one of a plurality of layered absorbent components having a liquid-absorbent layer, and which is positioned in a bottom stage having a clothing-facing surface provided with positioning-fixing means fixed to a piece of clothing, and having a skin-facing surface on the opposite side from the clothing-facing surface;
an upper absorbent component which is one of the plurality of layered absorbent components, and which is layered on the skin-facing surface of the bottom absorbent component; and
a temporal adhesive member which temporarily fixes the bottom absorbent component and the upper absorbent component layered and fixed together in a plurality of layers, and which is provided in the area in which the plurality of layers are layered and fixed;
wherein an adhesive strength of the temporal adhesive member between the absorbent components is lower than a fixing strength between each of the plurality of layers constituting the bottom absorbent component and than the fixing strength between each of the plurality of layers constituting the upper absorbent component,
wherein each of the plurality of layered absorbent components is of substantially the same width, and
wherein each of the bottom and upper absorbent components has a center portion and an end portion in the longitudinal direction, and the upper absorbent component's center portion and end portion are different in thickness from each other, and the bottom absorbent component's center portion and end portion are of substantially the same thickness.

13. The absorbent article according to claim 12, wherein the temporal adhesive member is formed in a position towards the inside from the edge of the absorbent component.

14. The absorbent article according to claim 12, wherein the temporal adhesive member is formed so as to have an excluded portion.

15. The absorbent article according to claim 14, wherein the bottom absorbent component and the upper absorbent component each have four corners, and the plane pattern of the temporal adhesive member is curved at the tip of each of the four corners.

16. The absorbent article according to claim 14, wherein the upper absorbent component is partially compressed in the excluded portion.

17. The absorbent article according to claim 12, wherein non-fusible fibers are included in at least one surface selected from the skin-facing surface of the bottom absorbent component and the clothing-facing surface of the upper absorbent component, and the temporal adhesive member is pressed in the thickness direction, heated, and formed in a state in which the skin-facing surface and the clothing-facing surface are placed opposite each other.

18. The absorbent article according to claim 1, wherein an embossed pattern is formed in at least one surface selected from the skin-facing surface of the bottom absorbent component and the skin-facing surface of the upper absorbent component, and mutually different patterns are provided on the skin-facing surfaces.

19. The absorbent article according to claim 1, wherein at least one functional agent selected from the group consisting of an antimicrobial agent, a deodorant, and a fragrance is included in at least the bottom absorbent component.

20. The absorbent article according to claim 1, wherein at least the bottom absorbent component has at least one functional agent selected from the group consisting of an antimicrobial agent, a deodorant, and a fragrance; and a tea-leaf extract is included as the functional agent.

* * * * *